United States Patent
Strobl et al.

(10) Patent No.: US 9,700,333 B2
(45) Date of Patent: *Jul. 11, 2017

(54) SURGICAL INSTRUMENT WITH VARIABLE TISSUE COMPRESSION

(71) Applicant: Ethicon LLC, Guaynabo, PR (US)

(72) Inventors: Geoffrey S. Strobl, Williamsburg, OH (US); Chad P. Boudreaux, Cincinnati, OH (US); Mark A. Davison, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/319,915

(22) Filed: Jun. 30, 2014

(65) Prior Publication Data

US 2015/0374396 A1    Dec. 31, 2015

(51) Int. Cl.
*A61B 17/285* (2006.01)
*A61B 17/28* (2006.01)
(Continued)

(52) U.S. Cl.
CPC .......... *A61B 17/282* (2013.01); *A61B 17/285* (2013.01); *A61B 18/1445* (2013.01);
(Continued)

(58) Field of Classification Search
CPC .. A61B 2017/2932; A61B 2018/00607; A61B 2018/1455; A61B 18/1445;
(Continued)

(56) References Cited

U.S. PATENT DOCUMENTS

| 2,366,274 A | 1/1945 | Luth et al. |
|---|---|---|
| 2,458,152 A | 1/1949 | Eakins |

(Continued)

FOREIGN PATENT DOCUMENTS

| DE | 43 00 307 A1 | 7/1994 |
|---|---|---|
| DE | 196 08 716 C1 | 4/1997 |

(Continued)

OTHER PUBLICATIONS

AST Products, Inc., "Principles of Video Contact Angle Analysis," 20 pages, (2006).

(Continued)

*Primary Examiner* — Jocelyn D Ram
(74) *Attorney, Agent, or Firm* — Mintz Levin Cohn Ferris Glovsky and Popeo, P.C.

(57) ABSTRACT

Surgical instruments and methods for applying variable compression to tissue are described herein and can have particular utility when cutting and sealing tissue. In one embodiment, a surgical instrument end effector is described that includes first and second jaw members movable relative to one another between an open position and a closed position to clamp tissue therebetween. The end effector can include a compression member configured to translate along the end effector to move the first and second jaw members and apply a variable compression force to the tissue. The variable compression force can have different profiles along the length of the end effector, including, for example, a continuously increasing profile or a profile that alternates between different values. The provided variable compression can reduce the force required to actuate the surgical instrument and increase the quality of a tissue seal formed thereby.

18 Claims, 14 Drawing Sheets

(51) Int. Cl.
  *A61B 17/072*  (2006.01)
  *A61B 17/29*  (2006.01)
  *A61B 18/14*  (2006.01)

(52) U.S. Cl.
  CPC .............. *A61B 2017/07257* (2013.01); *A61B 2017/07285* (2013.01); *A61B 2017/2933* (2013.01); *A61B 2018/1455* (2013.01)

(58) Field of Classification Search
  CPC .................. A61B 18/085; A61B 17/29; A61B 2017/2926; A61B 17/295; A61B 2017/2933
  USPC ...................................... 606/51, 52, 37, 207
  See application file for complete search history.

(56) References Cited

U.S. PATENT DOCUMENTS

| | | |
|---|---|---|
| 2,510,693 A | 6/1950 | Green et al. |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,166,971 A | 1/1965 | Stoecker |
| 3,525,912 A | 8/1970 | Wallin |
| 3,526,219 A | 9/1970 | Balamuth |
| 3,580,841 A | 5/1971 | Cadotte et al. |
| 3,636,943 A | 1/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,918,442 A | 11/1975 | Nikolaev et al. |
| 3,956,826 A | 5/1976 | Perdreaux, Jr. |
| 4,005,714 A | 2/1977 | Hiltebrandt |
| 4,034,762 A | 7/1977 | Cosens et al. |
| 4,058,126 A | 11/1977 | Leveen |
| 4,156,187 A | 5/1979 | Murry et al. |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,634,420 A | 1/1987 | Spinosa et al. |
| 4,640,279 A | 2/1987 | Beard |
| 4,708,127 A | 11/1987 | Abdelghani |
| 4,735,603 A | 4/1988 | Goodson et al. |
| 4,761,871 A | 8/1988 | O'Connor et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,920,978 A | 5/1990 | Colvin |
| 4,922,902 A | 5/1990 | Wuchinich et al. |
| 4,936,842 A | 6/1990 | D'Amelio et al. |
| 4,981,756 A | 1/1991 | Rhandhawa |
| 5,020,514 A | 6/1991 | Heckele |
| 5,026,387 A | 6/1991 | Thomas |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,190,541 A | 3/1993 | Abele et al. |
| 5,196,007 A | 3/1993 | Ellman et al. |
| 5,205,459 A | 4/1993 | Brinkerhoff et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,241,968 A | 9/1993 | Slater |
| 5,257,988 A | 11/1993 | L'Esperance, Jr. |
| 5,258,006 A | 11/1993 | Rydell et al. |
| 5,261,922 A | 11/1993 | Hood |
| 5,263,957 A | 11/1993 | Davison |
| 5,282,800 A | 2/1994 | Foshee et al. |
| 5,285,945 A | 2/1994 | Brinkerhoff et al. |
| 5,290,286 A | 3/1994 | Parins |
| D347,474 S | 5/1994 | Olson |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,346,502 A | 9/1994 | Estabrook et al. |
| 5,361,583 A | 11/1994 | Huitema |
| 5,366,466 A | 11/1994 | Christian et al. |
| D354,564 S | 1/1995 | Medema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,449,370 A | 9/1995 | Vaitekunas |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |

(56) References Cited

U.S. PATENT DOCUMENTS

| | | |
|---|---|---|
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,562,609 A | 10/1996 | Brumbach |
| 5,562,610 A | 10/1996 | Brumbach |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,647,871 A | 7/1997 | Levine et al. |
| 5,653,713 A | 8/1997 | Michelson |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,891,142 A | 4/1999 | Eggers et al. |
| 5,893,835 A | 4/1999 | Witt et al. |
| 5,897,569 A | 4/1999 | Kellogg et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,274 A | 11/1999 | Davison et al. |
| 5,989,275 A | 11/1999 | Estabrook et al. |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| H1904 H | 10/2000 | Yates et al. |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,844 B1 | 3/2001 | Reichel et al. |
| 6,206,876 B1 | 3/2001 | Levine et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,259,230 B1 | 7/2001 | Chou |
| 6,267,761 B1 | 7/2001 | Ryan |
| 6,273,852 B1 | 8/2001 | Lehe et al. |
| 6,274,963 B1 | 8/2001 | Estabrook et al. |

(56) References Cited

U.S. PATENT DOCUMENTS

| | | |
|---|---|---|
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,379,320 B1 | 4/2002 | Lafon et al. |
| 6,383,194 B1 | 5/2002 | Pothula |
| 6,387,109 B1 | 5/2002 | Davison et al. |
| 6,391,026 B1 | 5/2002 | Hung et al. |
| 6,391,042 B1 | 5/2002 | Cimino |
| 6,398,779 B1 | 6/2002 | Buysse et al. |
| H2037 H | 7/2002 | Yates et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,142 B1 | 10/2002 | Faller et al. |
| 6,464,689 B1 | 10/2002 | Qin et al. |
| 6,464,702 B2 | 10/2002 | Schulze et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,456 B1 | 4/2003 | Freeman |
| 6,544,260 B1 | 4/2003 | Markel et al. |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Lands et al. |
| 6,589,200 B1 | 7/2003 | Schwemberger et al. |
| 6,589,239 B2 | 7/2003 | Khandkar et al. |
| 6,602,252 B2 | 8/2003 | Mollenauer |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,544 B2 | 1/2004 | Mastri et al. |
| 6,695,840 B2 | 2/2004 | Schulze |
| 6,716,215 B1 | 4/2004 | David et al. |
| 6,722,552 B2 | 4/2004 | Fenton, Jr. |
| 6,733,506 B1 | 5/2004 | McDevitt et al. |
| 6,746,443 B1 | 6/2004 | Morley et al. |
| 6,752,815 B2 | 6/2004 | Beaupre |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,773,444 B2 | 8/2004 | Messerly |
| 6,775,575 B2 | 8/2004 | Bommannan et al. |
| 6,783,524 B2 | 8/2004 | Anderson et al. |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,828,712 B2 | 12/2004 | Battaglin et al. |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| D509,589 S | 9/2005 | Wells |
| 6,945,981 B2 | 9/2005 | Donofrio et al. |
| 6,953,461 B2 | 10/2005 | McClurken et al. |
| D511,145 S | 11/2005 | Donofrio et al. |
| 6,976,969 B2 | 12/2005 | Messerly |
| 6,977,495 B2 | 12/2005 | Donofrio |
| 6,984,220 B2 | 1/2006 | Wuchinich |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,088 B2 | 5/2006 | Nawrocki et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,125,409 B2 | 10/2006 | Truckai et al. |

(56) References Cited

U.S. PATENT DOCUMENTS

| | | |
|---|---|---|
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,163,548 B2 | 1/2007 | Stulen et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,204,820 B2 | 4/2007 | Akahoshi |
| 7,207,471 B2 | 4/2007 | Heinrich et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,331,410 B2 | 2/2008 | Yong et al. |
| 7,347,863 B2 | 3/2008 | Rothe et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,567,012 B2 | 7/2009 | Namikawa |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |

(56) References Cited

U.S. PATENT DOCUMENTS

| | | |
|---|---|---|
| 7,861,906 B2 | 1/2011 | Doll et al. |
| D631,965 S | 2/2011 | Price et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,901,423 B2 | 3/2011 | Stulen et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,039,705 B2 | 5/2015 | Takashino |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,119,957 B2 | 9/2015 | Gantz et al. |

(56) References Cited

U.S. PATENT DOCUMENTS

| | | |
|---|---|---|
| 9,125,662 B2 | 9/2015 | Shelton, IV |
| 9,149,325 B2 * | 10/2015 | Worrell .............. A61B 18/1445 |
| 9,168,085 B2 | 10/2015 | Juzkiw et al. |
| 9,179,912 B2 | 11/2015 | Yates et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 2001/0025184 A1 | 9/2001 | Messerly |
| 2001/0039419 A1 | 11/2001 | Francischelli et al. |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0115997 A1 | 8/2002 | Truckai et al. |
| 2002/0120266 A1 | 8/2002 | Truckai et al. |
| 2002/0156493 A1 | 10/2002 | Houser et al. |
| 2002/0165541 A1 | 11/2002 | Whitman |
| 2003/0014053 A1 | 1/2003 | Nguyen et al. |
| 2003/0055443 A1 | 3/2003 | Spotnitz |
| 2003/0105474 A1 | 6/2003 | Bonutti |
| 2003/0114851 A1 * | 6/2003 | Truckai .............. A61B 18/1445 606/51 |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0199870 A1 | 10/2003 | Truckai et al. |
| 2003/0204199 A1 | 10/2003 | Novak et al. |
| 2003/0212332 A1 | 11/2003 | Fenton et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0097919 A1 | 5/2004 | Wellman et al. |
| 2004/0097996 A1 | 5/2004 | Rabiner et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0204728 A1 | 10/2004 | Haefner |
| 2004/0232196 A1 | 11/2004 | Shelton et al. |
| 2004/0232197 A1 | 11/2004 | Shelton et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0049546 A1 | 3/2005 | Messerly et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0143769 A1 | 6/2005 | White et al. |
| 2005/0165345 A1 | 7/2005 | Laufer et al. |
| 2005/0165429 A1 | 7/2005 | Douglas et al. |
| 2005/0171522 A1 | 8/2005 | Christopherson |
| 2005/0171535 A1 | 8/2005 | Truckai et al. |
| 2005/0177184 A1 | 8/2005 | Easley |
| 2005/0192610 A1 | 9/2005 | Houser et al. |
| 2005/0203507 A1 | 9/2005 | Truckai et al. |
| 2005/0209620 A1 | 9/2005 | Du et al. |
| 2005/0251157 A1 | 11/2005 | Saadat et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0267464 A1 | 12/2005 | Truckai et al. |
| 2005/0288659 A1 | 12/2005 | Kimura et al. |
| 2006/0030797 A1 | 2/2006 | Zhou et al. |
| 2006/0052778 A1 | 3/2006 | Chapman et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0069388 A1 | 3/2006 | Truckai et al. |
| 2006/0079878 A1 | 4/2006 | Houser |
| 2006/0084963 A1 | 4/2006 | Messerly |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0027469 A1 | 2/2007 | Smith et al. |
| 2007/0055228 A1 | 3/2007 | Berg et al. |
| 2007/0060915 A1 | 3/2007 | Kucklick |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0146113 A1 | 6/2007 | Truckai et al. |
| 2007/0149881 A1 | 6/2007 | Rabin |
| 2007/0162050 A1 | 7/2007 | Sartor |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton et al. |
| 2007/0185380 A1 | 8/2007 | Kucklick |
| 2007/0185474 A1 | 8/2007 | Nahen |
| 2007/0191713 A1 | 8/2007 | Eichmann et al. |
| 2007/0191830 A1 | 8/2007 | Crompton et al. |
| 2007/0203483 A1 | 8/2007 | Kim et al. |
| 2007/0208312 A1 | 9/2007 | Norton et al. |
| 2007/0219481 A1 | 9/2007 | Babaev |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0015575 A1 | 1/2008 | Odom et al. |
| 2008/0027427 A1 | 1/2008 | Falkenstein et al. |
| 2008/0058585 A1 | 3/2008 | Novak et al. |
| 2008/0058775 A1 | 3/2008 | Darian et al. |
| 2008/0058802 A1 | 3/2008 | Couture et al. |
| 2008/0058845 A1 | 3/2008 | Shimizu et al. |
| 2008/0071268 A1 | 3/2008 | Hafner |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |

(56) References Cited

U.S. PATENT DOCUMENTS

| | | |
|---|---|---|
| 2008/0172051 A1 | 7/2008 | Masuda et al. |
| 2008/0177268 A1 | 7/2008 | Daum et al. |
| 2008/0188755 A1 | 8/2008 | Hart |
| 2008/0188851 A1 | 8/2008 | Truckai et al. |
| 2008/0188878 A1 | 8/2008 | Young |
| 2008/0188912 A1 | 8/2008 | Stone et al. |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0221565 A1 | 9/2008 | Eder et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0249527 A1 | 10/2008 | Couture |
| 2008/0262490 A1 | 10/2008 | Williams |
| 2008/0262491 A1 | 10/2008 | Swoyer et al. |
| 2008/0269862 A1 | 10/2008 | Elmouelhi et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0024144 A1 | 1/2009 | Zeiner et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082716 A1 | 3/2009 | Akahoshi |
| 2009/0099582 A1 | 4/2009 | Isaacs et al. |
| 2009/0105750 A1 | 4/2009 | Price et al. |
| 2009/0112229 A1 | 4/2009 | Omori et al. |
| 2009/0118802 A1 | 5/2009 | Mioduski et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0143795 A1 | 6/2009 | Robertson |
| 2009/0143806 A1 | 6/2009 | Witt et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0057084 A1 | 3/2010 | Hanna |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0179577 A1 | 7/2010 | Houser |
| 2010/0187283 A1 | 7/2010 | Crainich et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0087256 A1 | 4/2011 | Wiener et al. |
| 2011/0118754 A1 | 5/2011 | Dachs, II et al. |
| 2011/0155781 A1 | 6/2011 | Swensgard et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0224668 A1 | 9/2011 | Johnson et al. |
| 2011/0238065 A1* | 9/2011 | Hunt .................. A61B 17/295 606/45 |
| 2011/0251608 A1* | 10/2011 | Timm ................. A61B 17/295 606/41 |
| 2011/0251609 A1* | 10/2011 | Johnson ............. A61B 17/2804 606/46 |
| 2011/0251612 A1* | 10/2011 | Faller ................. A61B 18/1445 606/52 |
| 2011/0276049 A1 | 11/2011 | Gerhardt |
| 2011/0276057 A1 | 11/2011 | Conlon et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301602 A1* | 12/2011 | Roy ..................... A61B 17/29 606/51 |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0010616 A1 | 1/2012 | Huang et al. |
| 2012/0016413 A1 | 1/2012 | Timm et al. |
| 2012/0022519 A1 | 1/2012 | Huang et al. |
| 2012/0022525 A1 | 1/2012 | Dietz et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1* | 4/2012 | Davison ............. A61B 18/1445 606/45 |
| 2012/0083784 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2013/0023925 A1 | 1/2013 | Mueller |
| 2013/0030433 A1 | 1/2013 | Heard |
| 2013/0079762 A1 | 3/2013 | Twomey et al. |

(56) References Cited

U.S. PATENT DOCUMENTS

| | | |
|---|---|---|
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0193186 A1 | 8/2013 | (Tarinelli) Racenet et al. |
| 2013/0253256 A1 | 9/2013 | Griffith et al. |
| 2013/0253502 A1 | 9/2013 | Aronow et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0148806 A1 | 5/2014 | Witt et al. |
| 2014/0151428 A1* | 6/2014 | Boudreaux ........ A61B 18/1445 227/175.1 |
| 2014/0155878 A1* | 6/2014 | Trees .................. A61B 17/295 606/33 |
| 2014/0194874 A1* | 7/2014 | Dietz ................ A61B 18/1445 606/45 |
| 2014/0194915 A1 | 7/2014 | Johnson et al. |
| 2014/0257284 A1 | 9/2014 | Artale |
| 2014/0316408 A1 | 10/2014 | Davison et al. |
| 2014/0330271 A1 | 11/2014 | Dietz et al. |
| 2014/0336628 A1* | 11/2014 | McFarland ........ A61B 18/1445 606/33 |
| 2014/0336629 A1* | 11/2014 | Scheib ........... A61B 17/320016 606/33 |
| 2014/0343550 A1 | 11/2014 | Faller et al. |
| 2015/0025571 A1 | 1/2015 | Suzuki et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2015/0374396 A1 | 12/2015 | Strobl et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |

FOREIGN PATENT DOCUMENTS

| | | |
|---|---|---|
| DE | 296 23 113 U1 | 10/1997 |
| DE | 200 04 812 U1 | 9/2000 |
| DE | 102 01 569 A1 | 7/2003 |
| EP | 0 443 256 A1 | 8/1991 |
| EP | 0 456 470 A1 | 11/1991 |
| EP | 0 482 195 A1 | 4/1992 |
| EP | 0 340 803 B1 | 8/1993 |
| EP | 0 612 570 A2 | 8/1994 |
| EP | 0 705 571 A1 | 4/1996 |
| EP | 0 557 806 B1 | 5/1998 |
| EP | 0 908 148 A1 | 4/1999 |
| EP | 0 640 317 B1 | 9/1999 |
| EP | 1 199 044 A1 | 4/2002 |
| EP | 0 722 696 B1 | 12/2002 |
| EP | 1 293 172 B1 | 4/2006 |
| EP | 1 704 824 A1 | 9/2006 |
| EP | 1 749 479 A1 | 2/2007 |
| EP | 1 767 157 A1 | 3/2007 |
| EP | 1 832 259 A1 | 9/2007 |
| EP | 1 844 720 A1 | 10/2007 |
| EP | 1 862 133 A1 | 12/2007 |
| EP | 1 878 399 A1 | 1/2008 |
| EP | 1 915 953 A1 | 4/2008 |
| EP | 1 532 933 B1 | 5/2008 |
| EP | 1 707 143 B1 | 6/2008 |
| EP | 1 943 957 A2 | 7/2008 |
| EP | 1 974 771 A1 | 10/2008 |
| EP | 1 435 852 B1 | 12/2008 |
| EP | 1 849 424 B1 | 4/2009 |
| EP | 2 042 117 A1 | 4/2009 |
| EP | 2 060 238 A1 | 5/2009 |
| EP | 2 074 959 A1 | 7/2009 |
| EP | 1 810 625 B1 | 8/2009 |
| EP | 2 090 238 A1 | 8/2009 |
| EP | 2 090 256 A2 | 8/2009 |
| EP | 2 092 905 A1 | 8/2009 |
| EP | 2 105 104 A2 | 9/2009 |
| EP | 1 747 761 B1 | 10/2009 |
| EP | 1 769 766 B1 | 2/2010 |
| EP | 2 151 204 A1 | 2/2010 |
| EP | 2 153 791 A1 | 2/2010 |
| EP | 2 243 439 A1 | 10/2010 |
| EP | 1 510 178 B1 | 6/2011 |
| EP | 1 728 475 B1 | 8/2011 |
| EP | 2 353 518 A1 | 8/2011 |
| EP | 2 316 359 B1 | 3/2013 |
| EP | 2 578 172 A2 | 4/2013 |
| EP | 2 508 143 B1 | 2/2014 |
| GB | 2 472 216 A | 2/2011 |
| JP | 08-229050 A | 9/1996 |
| JP | 2008-018226 A | 1/2008 |
| JP | 2008-055167 A | 3/2008 |
| JP | 2008-508965 A | 3/2008 |
| JP | 2008-253781 A | 10/2008 |
| JP | 2010-051802 A | 3/2010 |
| JP | 5714508 B2 | 5/2015 |
| WO | 81/03272 A1 | 11/1981 |
| WO | 92/22259 A2 | 12/1992 |
| WO | 93/07817 A1 | 4/1993 |
| WO | 0 630 612 A1 | 12/1994 |
| WO | 98/37815 A1 | 9/1998 |
| WO | 00/24330 A1 | 5/2000 |
| WO | 00/24331 A1 | 5/2000 |
| WO | 00/25691 A1 | 5/2000 |
| WO | 01/28444 A1 | 4/2001 |
| WO | 01/54590 A1 | 8/2001 |
| WO | 02/062241 A1 | 8/2002 |
| WO | 02/080797 A1 | 10/2002 |
| WO | 03/001986 A2 | 1/2003 |
| WO | 03/013374 A1 | 2/2003 |
| WO | 03/020339 A2 | 3/2003 |
| WO | 03/028541 A2 | 4/2003 |

(56) References Cited

FOREIGN PATENT DOCUMENTS

| WO | 03/030708 | A2 | 4/2003 |
|---|---|---|---|
| WO | 03/068046 | A2 | 8/2003 |
| WO | 2004/011037 | A2 | 2/2004 |
| WO | 2004/032754 | A2 | 4/2004 |
| WO | 2004/032762 | A1 | 4/2004 |
| WO | 2004/032763 | A2 | 4/2004 |
| WO | 2004/078051 | A2 | 9/2004 |
| WO | 2004/112618 | A2 | 12/2004 |
| WO | 2005/052959 | A2 | 6/2005 |
| WO | 2005/122917 | A1 | 12/2005 |
| WO | 2006/021269 | A1 | 3/2006 |
| WO | 2006/036706 | A1 | 4/2006 |
| WO | 2006/042210 | A2 | 4/2006 |
| WO | 2006/055166 | A2 | 5/2006 |
| WO | 2006/119139 | A2 | 11/2006 |
| WO | 2006129465 | | 12/2006 |
| WO | 2007/047531 | A2 | 4/2007 |
| WO | 2007/143665 | A2 | 12/2007 |
| WO | 2008/020964 | A2 | 2/2008 |
| WO | 2008/045348 | A2 | 4/2008 |
| WO | 2008/099529 | A1 | 8/2008 |
| WO | 2008/101356 | A1 | 8/2008 |
| WO | 2009/022614 | A1 | 2/2009 |
| WO | 2009/027065 | A1 | 3/2009 |
| WO | 2009/036818 | A1 | 3/2009 |
| WO | 2009/039179 | A1 | 3/2009 |
| WO | 2009/059741 | A1 | 5/2009 |
| WO | 2009/082477 | A2 | 7/2009 |
| WO | 2009/149234 | A1 | 12/2009 |
| WO | 2010/017266 | A1 | 2/2010 |
| WO | 2010/090835 | A1 | 8/2010 |
| WO | 2010/104755 | A1 | 9/2010 |
| WO | 2011/084768 | A1 | 7/2011 |
| WO | 2011/089717 | A1 | 7/2011 |
| WO | 2011/144911 | A1 | 11/2011 |
| WO | 2012/044606 | A2 | 4/2012 |
| WO | 2012/166510 | A1 | 12/2012 |
| WO | 2013/034629 | A1 | 3/2013 |
| WO | 2013/062978 | A2 | 5/2013 |
| WO | 2013/154157 | A1 | 10/2013 |
| WO | 2015/197395 | A1 | 12/2015 |

OTHER PUBLICATIONS

[NoAuthorListed]Technology Overview, Printed from www.harmonicscalpel.com, Internet site, website accessed on Jun. 13, 2007, (3 Pages).
Campbell et al, "Thermal Imaging in Surgery," p. 19-23, in Medical Infrared Imaging, N.A. Diakides and J.D. Bronzino, Eds. (2008)(4 pages).
Duck, F.A., "Optical Properties of Tissue Including Ultraviolet and Infrared Radiation," pp. 43-71 in Physical Properties of Tissue (1990)(19 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
International Search Report for PCT/US2011/053413, dated Jul. 2, 2013 (4 pages).
Written Opinion for PCT/US2011/053413, dated Jul. 2, 2013 (4 pages).
Lim et al., "A Review of Mechanism Used in Laparoscopic Surgical Instruments," Mechanism and Machine Theory, vol. 38, pp. 1133-1147, (2003).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995)(10 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
[No Author Listed] Covidien Brochure, The LigaSure™ 5 mm Blunt Tip Sealer/Divider Family, dated Apr. 2013 (2 pages).
[No Author Listed] Covidien Brochure, [Value Analysis Brief], LigaSure Advance™ Pistol Grip, dated Apr. 2010 (7 pages).
[No Author Listed] Covidien Brochure, LigaSure Atlas™ Hand Switching Instruments, dated Dec. 2008 (2 pages).
[No Author Listed] Covidien Brochure, LigaSure Impact™ Instrument LF4318, dated Feb. 2013 (3 pages).
[No Author Listed] Covidien Brochure, The LigaSure Precise™ Instrument, dated Mar. 2011 (2 pages).
[No Author Listed] Erbe Electrosurgery VIO® 200 S, (2012), 12 pages, accessed Mar. 31, 2014 at http://www.erbe-med.com/erbe/media/Marketingmaterialien/85140-170_ERBE_EN_VIO_200_S_D027541.
[No Author Listed] The K&J Magnetic Field Calculator. K&J Magnetics, Inc., https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp, 4 pages.
[No Author Listed] National Semiconductors Temperature Sensor Handbook, 1994-1997, 40 pages—http://www.national.com/appinfo/tempsensors/files/temphb.pdf; accessed online: Apr. 1, 2011.
Amoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, Journal of Biomechanical Engineering, vol. 119, pp. 372-378 (Nov. 1997).
Chen et al., "Heat-Induced Changes in the Mechanics of a Collagenous Tissue: Isothermal, Isotonic Shrinkage," Transactions of the ASME, Journal of Biomechanical Engineering, vol. 120, pp. 382-388 (Jun. 1998).
Chen et al., "Heat-induced changes in the mechanics of a collagenous tissue: pseudoelastic behavior at 37° C.," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Douglas, S.C. "Introduction to Adaptive Filters". Digital Signal Processing Handbook. Eds. Vijay K. Madisetti and Douglas B. Williams. Boca Raton: CRC Press LLC, 1999, Ch. 18, 19 pages.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001), 2 pages.
Glaser and Subak-Sharpe, Integrated Circuit Engineering, Addison-Wesley Publishing, Reading, MA (1979). (book—not attached).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury, V. The predictability and the significance of thermally induced rate processes leading to irreversible epidermal injury." Archives of Pathology, 434, pp. 489-502 (1947).
Hormann et al., "Reversible and irreversible denaturation of collagen fibers." Biochemistry, 10, pp. 932-937 (1971).
Humphrey, J.D., "Continuum Thermomechanics and the Clinical Treatment of Disease and Injury," Appl. Mech. Rev., vol. 56, No. 2, pp. 231-260 (Mar. 2003).

(56) References Cited

OTHER PUBLICATIONS

Jang, J. et al. "Neuro-fuzzy and Soft Computing." Prentice Hall, 1997, pp. 13-89, 199-293, 335-393, 453-496, 535-549.
Gieck, Kurt & Reiner Gieck, Friction numbers, § Z.7, Engineering Formulas, (7th ed. 1997), 3 pages.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 381, pp. 248-255 (Dec. 2000).
Sullivan, "Optimal Choice for Number of Strands in a Litz-Wire Transformer Winding," IEEE Transactions on Power Electronics, vol. 14, No. 2, Mar. 1999, pp. 283-291.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
U.S. Appl. No. 12/576,529, filed Oct. 9, 2009, 18 pages.
Wall et al., "Thermal modification of collagen," J Shoulder Elbow Surg, No. 8, pp. 339-344 (Jul./Aug. 1999).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb., 1998. ASME Journal of Biomechanical Engineering, vol. 120, pp. 22-26.
Japanese Office Action for Appln. No. 2013-531709, issued Jun. 23, 2015 (12 pages).

* cited by examiner

SURGICAL INSTRUMENT WITH VARIABLE TISSUE COMPRESSION

FIELD

The present invention relates to surgical devices and, more particularly, to surgical devices for cutting and sealing tissue.

BACKGROUND

Surgical procedures often require the transection of tissue for a variety of purposes. In many cases, there is a need to both transect and seal tissue at the cutting site to prevent bleeding or fluid leakage from a luminal tissue structure being operated on. Accordingly, a number of devices exist for accomplishing these tasks, including devices configured for use in open surgery and minimally invasive procedures.

Many known devices include opposed jaw members configured to clamp tissue therebetween and a translating compression/cutting element that can drive the opposed jaw members to a closed position and also transect the tissue clamped between the jaw members. Sealing can likewise be accomplished in a variety of manners, including by the application of staples on either side of the compression/cutting element or the use of radio-frequency (RF) electrical or other energy to fuse the tissue together.

The opposed jaw members of some known devices may include one or more closure tracks that are configured to receive a portion of the compression/cutting element and guide the translation thereof along the jaw members. These closure tracks generally extend parallel to one another when the jaw members are in a closed position and are often arranged to provide for a desired gap between the jaw members when in the closed position.

There can be disadvantages to such devices, however. For example, a compression/cutting member can have a poor mechanical advantage when positioned close to a pivot joint of the jaw members, thereby requiring a large amount of force to compress tissue and advance along the jaw members. The poor mechanical advantage and large required force can make operation of the device difficult for users.

Additionally, in devices where RF or other energy delivery is used to seal tissue, forcing the actuation of the device can rush the procedure and transect the tissue before enough time has elapsed to sufficiently fuse the tissue. On the other hand, simply reducing the amount of compression provided in such devices can also be disadvantageous, because insufficient compression during sealing can lead to insufficient fusing of tissue. Insufficient sealing can cause bleeding from the transected tissue or leakage from a transected internal lumen or cavity.

Accordingly, there is a need for improved instruments and methods for applying variable compression to tissue to modulate required actuation forces during cutting and sealing operations. In particular, there is a need for improved instruments and methods that can reduce a required force to actuate an instrument while maintaining a desired level of compression and promoting effective sealing of tissue.

SUMMARY

The present invention generally provides surgical instruments and methods that employ variable tissue compression to address the shortcomings of the prior art. More particularly, the devices and methods described herein can modulate the compression force applied to tissue by an instrument to reduce a force required to actuate the instrument and allow for more effective sealing of tissue. In some embodiments, modulation can be accomplished by reducing an initial compression force applied to tissue and steadily increasing the compression force to a final value. In other embodiments, modulation can be accomplished by alternating between different compression levels (e.g., repeated alternation between higher and lower compression levels). Such variation in compression forces applied to tissue can be provided in a number of manners. In some embodiments, the instruments and methods of the present invention can include closure tracks extending along jaw members of an instrument that have variable profiles including sloped or curved portions. The various sloped or curved portions can allow a compression member to translate along the closure tracks with varying levels of resistance, thereby varying the force required to translate the compression member (i.e., the force required to actuate the device) and the compression force applied to the tissue through the jaw members.

In one aspect, a surgical end effector is provided that includes first and second jaw members movable relative to one another between an open position and a closed position to clamp tissue therebetween. The end effector also includes a first closure track formed in the first jaw member and extending along a length thereof, as well as a second closure track formed in the second jaw member and extending along a length thereof. The end effector further includes a compression member configured to translate longitudinally along a length of the end effector such that a first portion of the compression member contacts the first closure track and a second portion of the compression member contacts the second closure track to move the first jaw member and the second jaw member so as to apply compression to tissue disposed between the first and second jaw members as the compression member advances towards a distal end of the end effector. Still further, when the first and second jaw members are in the closed position, a distance between the first closure track and the second closure track increases continuously from a proximal-most end of the first closure track to a location adjacent to a distal end of the first closure track.

The devices and methods described herein can have a number of additional features and/or variations, all of which are within the scope of the present invention. For example, in some embodiments the distance between the first closure track and the second closure track can remain constant from the distal end of the first closure track to the location adjacent to the distal end of the first closure track. Such a feature can provide a flat region at the distal-most portion of the closure track to ensure that first and second jaws provide a desired level of compression to the tissue by the end of the compression member's translation. This feature can have particular utility in preventing distal tip bleeding or other tissue sealing complications from insufficient tissue compression.

In other embodiments, at least one of the first and second jaw members can include at least one electrode disposed on a surface thereof that is configured to contact tissue clamped between the first and second jaw members. In certain embodiments, for example, a single electrode can be disposed on either one of the first and second jaw members, while in other embodiments a plurality of electrodes can be disposed on both the first and second jaw members. In other embodiments, however, other sealing mechanisms can be employed, such as stapling cartridges, etc.

The first and second closure tracks of the end effector can have a variety of shapes. For example, in some embodiments the distance between the first closure track and the second closure track can increase linearly from the proximal-most end of the first closure track to the location adjacent to the distal end of the first closure track. In other words, the distance between the first and second closure tracks can increase continuously from a proximal-most end of the closure tracks to, for example, a point adjacent to a distal end of the closure tracks where a flat region can begin. In other embodiments, however, the distance can continuously increase from the proximal-most end to the distal end of the closure tracks. In still other embodiments, a profile of the distance between the first closure track and the second closure track between the proximal end of the first closure track and the location adjacent to the distal end of the first closure track can be curved or waveform-like.

The second closure track can also have a variety of shapes and profiles, depending on the particular embodiment. For example, a distance between the second closure track and a surface of the second jaw member that faces the first jaw member can remain constant from a proximal-most end of the second closure track to a distal end of the second closure track. Such an embodiment can be utilized, for example, if the second jaw member is fixed and the first jaw member moves relative thereto. The second closure track need not have such a flat profile, however, and in some embodiments a distance between the second closure track and a surface of the second jaw member that faces the first jaw member can vary from a proximal-most end of the second closure track to a distal end of the second closure track. A number of different track shapes or profiles are possible, similar to the first closure track described above. For example, in some embodiments a profile of the distance between the second closure track and the surface of the second jaw member can include at least one sloped or curved portion.

In another aspect, a surgical end effector is provided that includes first and second jaw members movable relative to one another between an open position and a closed position to clamp tissue therebetween. The end effector further includes a first closure track formed in the first jaw member and extending along a length thereof, as well as a second closure track formed in the second jaw member and extending along a length thereof. The end effector also includes a compression member configured to translate longitudinally along a length of the end effector such that a first portion of the compression member contacts the first closure track and a second portion of the compression member contacts the second closure track. Still further, a profile of at least one of the first closure track and the second closure track can be a wave function to vary an amount of compression applied to the tissue clamped between the first and second jaw members.

The wave function profile of the first and/or second closure track can have a variety of forms. For example, in some embodiments the profile of at least one of the first closure track and the second closure track can be a wave function having constant amplitude and frequency. In such an embodiment, a distance between the first closure track and the second closure track when the first and second jaw members are in the closed position can repeatedly and regularly alternate between a first distance and a second distance along a length of the end effector to vary an amount of compression applied to the tissue clamped between the first and second jaw members. Expressed another way, a profile of the distance between the first closure track and the second closure track can match a sinusoidal wave function, wherein a wavelength and amplitude is constant over a length of the first closure track.

In other embodiments, the profile of at least one of the first closure track and the second closure track can be a wave function having at least one of variable amplitude and variable frequency. In such embodiments, the distance between the first closure track and the second closure track when the first and second jaw members are in the closed position can alternate (regularly or irregularly) between a first distance and at least a second distance along a length of the end effector. In still other embodiments, the profile of at least one of the first closure track and the second closure track can be a wave function having both variable amplitude and variable frequency. By way of further example, in one embodiment the distance between the first closure track and the second closure track can alternate between a first distance, a second distance, and a third distance along the length of the end effector.

By varying the frequency and/or amplitude of the wave function defined by the closure track profile of the first jaw member and/or second jaw member, the distance between the jaw members can be varied along the length of the end effector. In some embodiments, for example, the second distance can be greater than the first distance, or vice versa. Further, if there is a third distance, as in the example above, the third distance can be greater than the second distance and the first distance in certain embodiments. Regardless, the variation in compression (e.g., alternation between higher and lower levels of compression) can modulate the amount of force required to actuate the end effector and, in certain embodiments, can promote better fusing of tissue during application of RF or other energy. In addition, in certain embodiments the end effector can be part of a larger surgical instrument, and can include a shaft extending proximally from the end effector, as well as a handle coupled to a proximal end of the shaft. The handle can include a trigger mechanism to cause the compression member to be translated along the end effector, deliver RF or other energy to seal tissue, etc.

In certain embodiments, the first closure track can include a flat distal-most portion that is traversed by the compression member after the alternations, similar to the flat portion described above. For example, the distance between the first closure track and the second closure track can remain constant from a distal end of the first closure track to a location adjacent to the distal end the first closure track.

As noted above, the regular or irregular alternation or oscillation between different distance values can be accomplished by varying the profiles of any of the first closure track and the second closure track. And any of the variations or modifications to the first and/or second closure track described herein can be applied in any combination to either closure track.

In another aspect, a method for actuating a surgical instrument is provided that includes positioning an end effector having first and second jaw members such that tissue is disposed within a gap between the first and second jaw members, and applying a continuously variable compression force to the tissue by advancing a compression member distally along a length of the end effector.

The method can also include a number of additional steps or variations, all of which are considered within the scope of the present invention. For example, in some embodiments the method can further include applying a constant compression force to the tissue as the compression member is advanced over a distal-most portion of the end effector. By way of further example, such a constant compression force can be provided by advancing the compression member over a distal-most flat portion (e.g., a portion parallel to a lower surface of the jaw member or a closure track of the opposing jaw member) of closure track, as described above.

In other embodiments, the continuously variable compression force applied to the tissue can continuously increase as the compression member is advanced distally along the length of the end effector. In certain other embodiments, however, the continuously variable compression force applied to the tissue can repeatedly alternate between a first value and a second value that is higher than the first value as the compression member is advanced distally along the length of the end effector. Any of the various modifications to a continuously increasing or repeatedly alternating compression force described above can be employed as well.

In still other embodiments, the method can further include delivering energy into the tissue from at least one electrode coupled to the end effector to seal the tissue. For example, at least one of the first and second jaw members can include at least one electrode coupled thereto that can be utilized to deliver energy into tissue clamped between the jaw members. In other embodiments, however, the method can also include delivering alternative sealing mechanisms into tissue, such as staples, etc.

As noted above, any of the additional features or variations described above can be applied to any particular aspect or embodiment of the invention in a number of different combinations; the absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to surgical devices and methods that are used in tissue cutting and sealing operations. The devices and methods described herein employ variable tissue compression during actuation to reduce the force required to actuate a surgical device and promote more effective sealing of tissue. In general, reducing the amount of compression provided when the device has a lower mechanical advantage over the tissue and increasing the amount of compression as the device's mechanical advantage increases can reduce the force required to actuate a surgical device. In other embodiments, however, the amount of compression can be repeatedly modulated between higher and lower values to both reduce the force required to actuate and to promote the formation of an effective tissue seal when applying RF energy.

Figure 1:
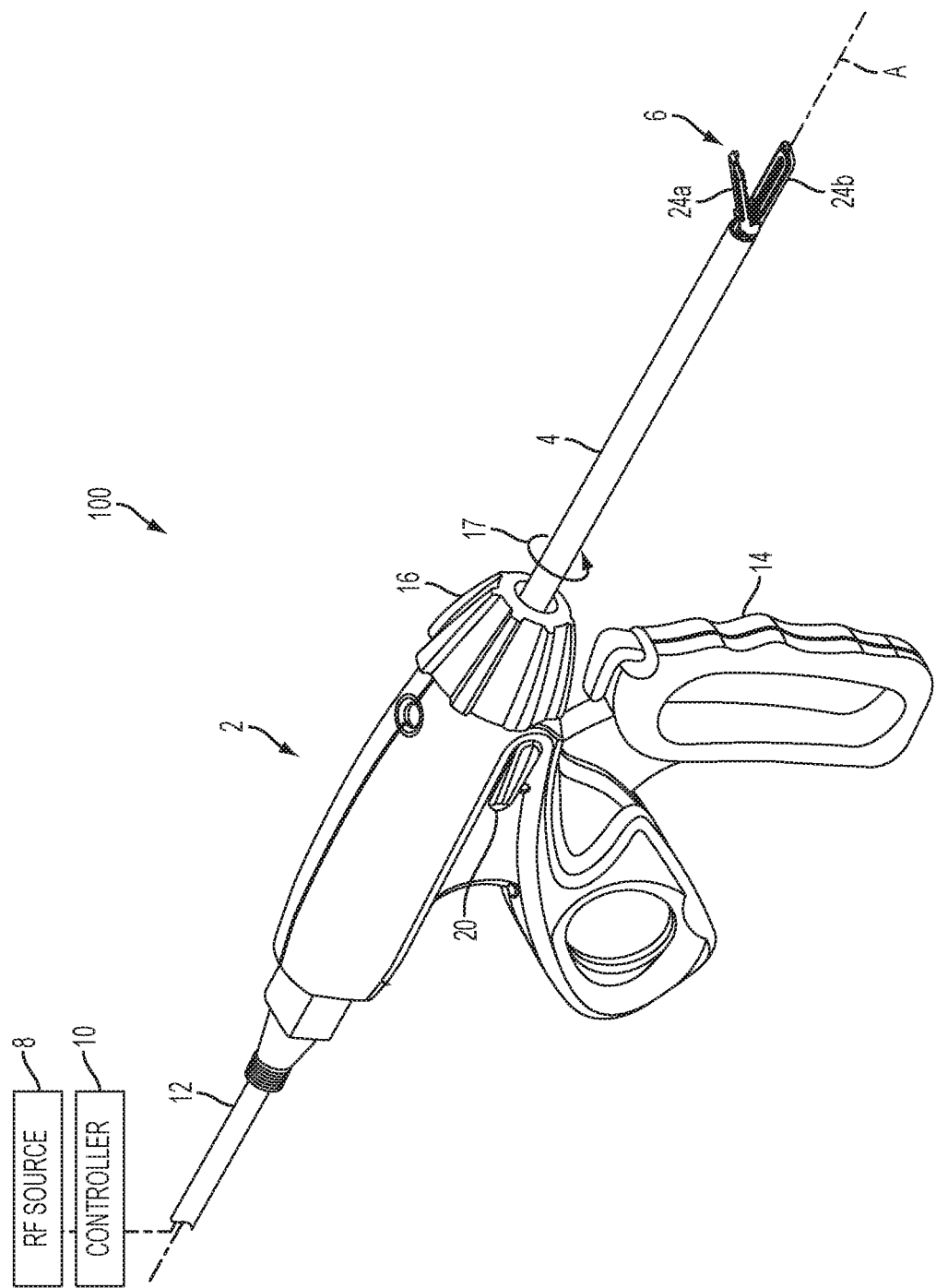
FIG. 1 is a perspective view of one embodiment of a surgical instrument for cutting and sealing tissue.

FIG. 1 shows one embodiment of a surgical instrument 100 that can be used to cut and seal tissue. The surgical instrument 100 can generally include a handle portion 2, a shaft 4, and an end effector 6. Manipulation of components of the handle portion 2 can be effective to manipulate the shaft 4 and/or the end effector 6 during an open or minimally invasive surgical procedure.

While a person having skill in the art will recognize that the size, shape, and configuration of each of the handle portion 2, shaft 4, and end effector 6 can depend, at least in part, on the size, shape, and configuration of the components used therewith and the type of procedure being performed, in the illustrated embodiment the handle portion 2 is of a pistol-grip nature and includes a first trigger 14 pivotally coupled to the handle portion 2. Pivotal movement of the trigger 14 towards the handle portion 2 can be effective to actuate the end effector 6, and thus as shown is effective to move jaws 24a, 24b of the end effector 6 from an open position (FIG. 2) to a closed position (FIG. 3). More particularly, movement of the trigger 14 can initiate one or more mechanical and/or electrical signals or processes that cause the actuation of the end effector 6. A person skilled in the art will recognize a variety of different mechanical and electrical components that can be associated with either or both of the handle portion 2 and the shaft 4 to assist in actuating the end effector 6. Further, in addition to being able to have a variety of sizes, shapes, and configurations, the handle portion 2 can also be made from a variety of materials. In one embodiment, for example, the handle portion 2 can be made from a generally rigid material such as a metal (e.g., stainless steel, titanium, etc.) or a rigid polymer.

In some embodiments the handle portion 2 can include a rotational control collar 16 that can be used to rotate the shaft 4 and/or the end effector 6. As shown, the collar 16 can be rotated about a longitudinal axis A, which in turn can rotate each of the shaft 4 and the end effector 6 a full 360 degrees about the longitudinal axis A, as shown by arrow 17. The first and second jaws 24a, 24b can remain operable to open and close while being rotated.

Further, in some embodiments a proximal end of the handle portion 2 can be coupled to a radio frequency (RF) or other energy source 8 and a controller 10 via a cable 12. The RF energy from the source 8 can be delivered through the handle to the end effector 6 for use in sealing tissue. An activation button 20 can be provided to initiate, for instance by completing a circuit, and/or otherwise control the application of RF energy to the instrument and thus tissue disposed in the jaws 24a, 24b. Alternatively, any combination of one or more activation buttons, the trigger 14, a foot pedal, and/or other known control devices can be used to initiate, apply, and/or otherwise control RF energy supplied for sealing tissue. In embodiments that do not use RF energy to seal tissue, the handle portion 2 can include other mechanical or electrical structures known to those skilled in the art to deliver other forms of tissue sealing, such as staples.

A person skilled in the art will recognize other non-limiting examples of features that can be incorporated with the handle portion 2 to assist in manipulating or otherwise operating the device include: (1) an articulation lever for articulating the end effector 6; (2) a retraction handle for retracting a cutting blade or compression member, such as the compression member 22 described further below, towards and/or to their initial positions in place of or independent of any retraction that is part of a firing stroke initiated by the trigger 2; (3) a firing lockout assembly to prevent a cutting blade or compression member from being actuated at an undesirable time; and (4) an emergency return button to retract a cutting blade or compression member before a firing stroke is completed, for instance in a case where completing the firing stroke may cause tissue to be undesirably cut. Although features such as an articulation lever, a retraction handle, a firing lockout assembly, and an emergency return button are not explicitly illustrated in the device 100, a person skilled in the art will recognize a variety of configurations for each feature that can be incorporated into the handle portion 2 and/or other portions of the device 100 without departing from the spirit of the present disclosure.

The shaft 4 can be removably coupled to the distal end of the handle portion 2 at a proximal end of the shaft 4 and can include an inner lumen extending therethrough for passing mechanisms to help actuate the jaws 24a, 24b, or to perform other functions at the surgical site, such as cutting or delivering electrical energy for sealing. By way of non-limiting examples, components such as an actuation rod, a cutting blade or compression member, leads, and other mechanical and/or electrical control can be associated with portions of the handle portion 2, extend through the inner lumen of the shaft 4 and to the end effector 6 to assist in the operation of the device 100 generally and the end effector 6 more specifically.

A distal end of the shaft 4 can be configured to receive the end effector 6 by any known means for coupling an end effector to a shaft, including by a removable connection that allows various end effectors to be removably and replaceably coupled to the distal end of the shaft 4. While the shaft 4 can have any number of shapes and configurations, depending, at least in part, on the configurations of the other device components with which it is used and the type of procedure in which the device is used, in the illustrated embodiment the shaft 4 is generally cylindrical and elongate.

In some embodiments, the shaft 4 can be formed from a rigid material, e.g., a metal such as stainless steel, titanium, etc., or a rigid polymer, while in other embodiments the shaft 4 can be formed from semi-rigid or flexible materials to allow for deformation when desired, such as during some types of minimally invasive procedure. Exemplary semi-rigid materials can include polypropylene, polyethylene, nylon, or any of a variety of other known materials. The shaft 4 can have any longitudinal length, although in some embodiments it can be long enough to allow the handle portion 2 to be manipulated outside a patient's body while the shaft 4 extends through an opening in the body to position the end effector 6 at a surgical site within the patient's body. The shaft 4 can similarly have any diameter but, in some embodiments, can have a diameter suited to introduction into a patient's body during a minimally invasive surgery.

Figure 2:
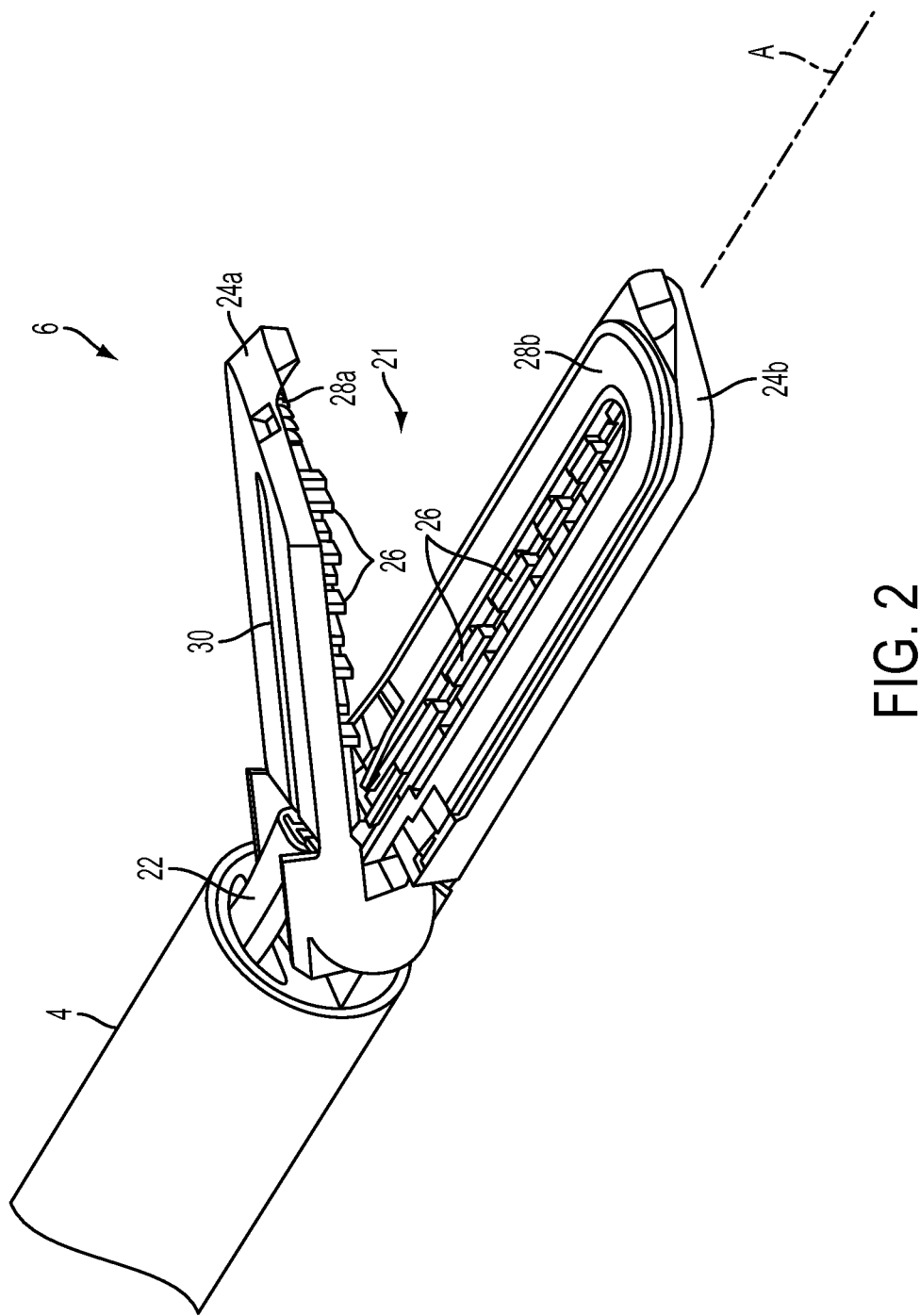
FIG. 2 is a perspective view of the end effector of the device shown in FIG. 1 in an open position.
Figure 3:
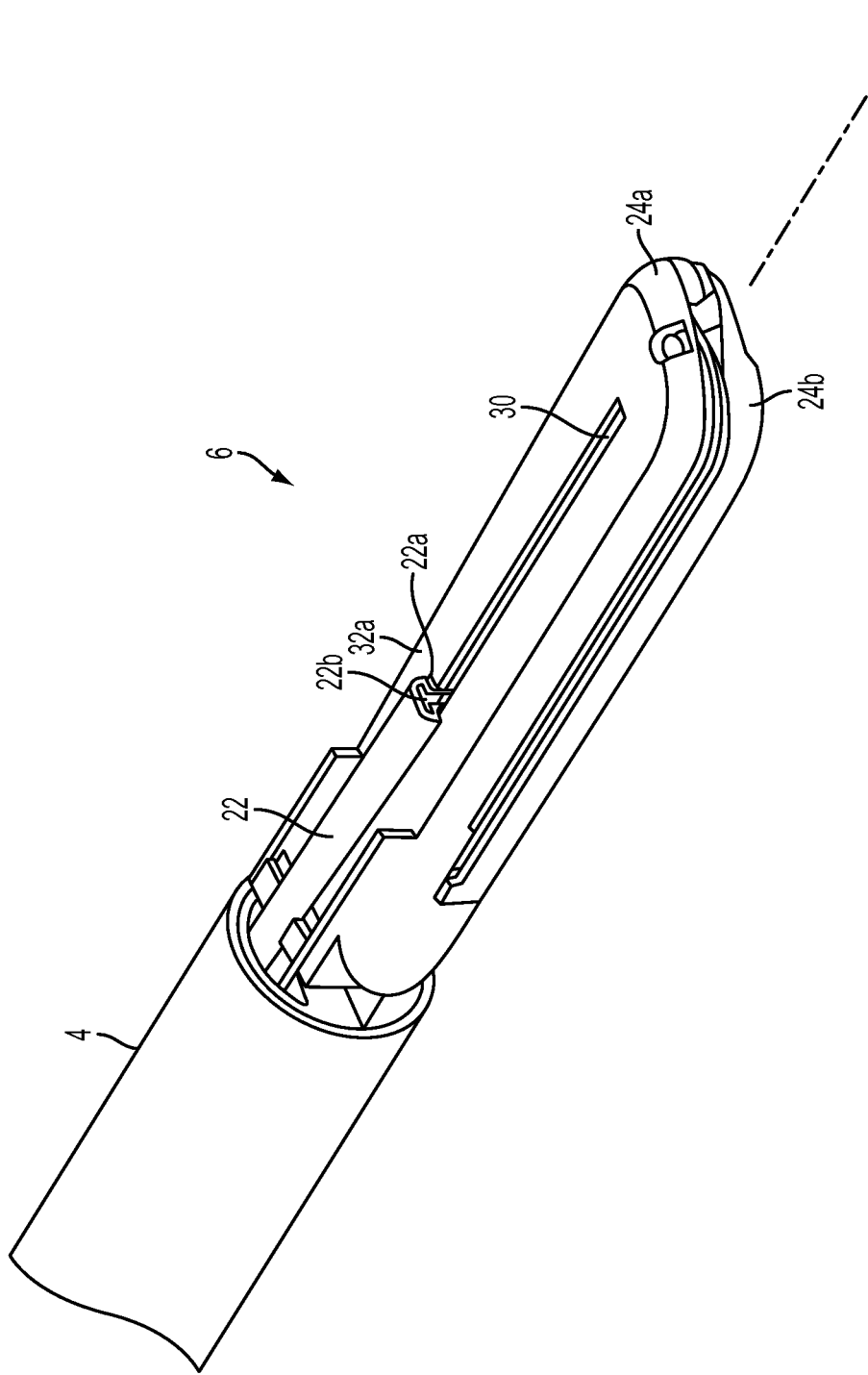
FIG. 3 is a perspective view of the end effector of the device shown in FIG. 1 in a closed position.

FIGS. 2 and 3 illustrate one, non-limiting embodiment of an end effector 6 that can be coupled to a distal end of the shaft 4. As shown the end effector 6 can include first and second jaw members 24a, 24b that are movable relative to one another between an open position, as shown in FIG. 2, and a closed position, as shown in FIG. 3, to clamp tissue disposed within a gap 21 therebetween. The first and second jaw members 24a, 24b can extend distally from a proximal end of the end effector and can be pivotably attached or otherwise coupled to one another. In some embodiments, one jaw member can be fixed while the other is configured to pivot, for instance the second jaw member 24b can be fixed relative to the end effector 6, such that closure of the end effector is accomplished by movement of the first jaw member 24a alone. In other embodiments, however, both the first and second jaw members 24a, 24b can be configured to pivot independently. Further, in some embodiments each jaw member 24a, 24b can include teeth 26 or other surface features (e.g., a textured or roughened surface) formed thereon to more effectively grip tissue when the jaw members are in the closed position. The end effector 6, and thus the jaws 24a, 24b and related components, can have a variety of sizes, shapes, and configurations, depending, at least in part, on the size, shape, and configuration of the components used therewith and the type of procedure being performed. In some embodiments, the end effector 6 can be sized such that the proximal end of the end effector can be telescopically received within the shaft during the operation, or the entire end effector 6 can be sized to be received within a trocar or other sleeve during introduction into a patient's body.

FIG. 2 illustrates the end effector 6 in an open position wherein the end effector can be positioned such that tissue is disposed between the first and second jaw members 24a, 24b. The first jaw member 24a can, in some embodiments, include a first energy delivery surface 28a (not visible) including at least one electrode. The second jaw member 24b can similarly include a second energy delivery surface 28b including at least one electrode. The first and second energy delivery surfaces 28a, 28b can have a variety of configurations. In one embodiment, the energy delivery surfaces 28a, 28b can extend in a "U" shape about the distal end of end effector 6, as shown in FIG. 2 with respect to the energy delivery surface 28b. The energy delivery surfaces 28a, 28b can provide a tissue contacting surface or surfaces for contacting, gripping, and/or manipulating tissue therebetween. As discussed above, the end effector 6 can be coupled to an RF energy source 8 via the shaft 4 and handle portion 2. In the illustrated embodiment, a user of the device 100 can press the activation button 20 which would signal the controller 10 to deliver RF energy to the energy delivery surfaces 28a, 28b, thereby sealing the tissue captured between the first and second jaw member 24a, 24b. While in the illustrated embodiment each jaw 24a, 24b is described as having an energy delivery surface 28a, 28b, in other embodiments only one jaw may have an energy delivery surface, or if the device is not configured to include energy delivery, neither jaw can have an energy delivery surface in some instances.

As just indicated, in some embodiments it may not be desirable to use RF energy to seal tissue, and thus energy delivery surfaces can not be included in some embodiments. A person skilled in the art will recognize that alternative tissue sealing mechanisms can be employed in conjunction with the disclosures provided for herein. By way of non-limiting example, in some embodiments, features such as an anvil and staple cartridge can be incorporated into the jaw members 24a, 24b to allow stapling to be performed by the end effector. In such an embodiment, the end effector 6 can contain a plurality of staples, which, upon the closure of the first and second jaw members 24a, 24b, can be delivered into tissue grasped between the jaw members. One or more rows and/or columns of staples can fired into tissue disposed between the jaw members 24a, 24b, as is known to those skilled in the art. More particularly, a first jaw member can include a plurality of staple forming pockets formed as part of an anvil and a second jaw member can include a plurality of staples held in a cartridge. Upon actuation, the staples can be ejected from the cartridge through the tissue disposed between the first and second jaw members. The staples can then abut against the staple-forming pockets in the second jaw member, which can close the staples and complete the tissue seal. U.S. Patent Publication No. 2004/0232197 to Shelton et al., which is hereby incorporated by reference in its entirety, provides some exemplary disclosures pertaining to end effectors that perform stapling and that can be used in conjunction with the disclosures provided for herein.

Movement of the first and second jaw members 24a, 24b between the closed and open positions described above can, in some embodiments, be controlled by a translating compression member 22. In the illustrated embodiment of FIGS. 1-3, the compression member 22 rides within a compression member cavity 30 that extends along the length of the first and second jaw members 24a, 24b. Extending the compression member 22 from a proximal end of the end effector 6 towards a distal end thereof can cause the first and second jaw members 24a, 24b to pivot toward one another, thereby applying a compression force to tissue disposed in the gap 21 therebetween. As is described in more detail below, continued distal translation of the compression member 22 can apply additional compressive force to the tissue disposed between the jaw members 24a, 24b. In some embodiments, the compression member can include a cutting blade formed on or otherwise located on a distal, leading end thereof such that translation of the compression member towards the distal end of the jaw members 24a, 24b can transect tissue disposed between the jaw members 24a, 24b. The transected tissue can subsequently be sealed using techniques described herein or otherwise known to those skilled in the art.

In other embodiments, a separate closure mechanism can be employed to move the first and second jaw members 24a, 24b between the open and closed positions, however, and the translating compression member can be actuated only after the jaw members have been brought to a substantially closed position by the separate closure mechanism. For example, U.S. patent application Ser. No. 14/075,839, filed Nov. 8, 2013, and entitled "Electrosurgical Devices," discloses an independent closure mechanism for moving jaw members from an open to a substantially closed position. The entire contents of this application are hereby incorporated by reference herein.

Returning to the compression member cavity 30, both the first and second jaw members 24a, 24b can include such a cavity that is sized to receive a compression member 22 when the compression member 22 is extended distally. FIGS. 2 and 3 illustrate one exemplary embodiment of a compression member 22. The compression member cavity 30 can extend along a length of each of the first and second jaw members 24a, 24b at a medial location to direct the compression member 22 as it is advanced from a proximal end to a distal end of the first and second jaw members. The compression member 22 can be guided by at least one closure track 32a, 32b defined in the sidewalls of the compression member cavity of each jaw member 24a, 24b. As the compression member 22 is actuated to translate along the longitudinal axis A of the end effector 6 through the channel 30, the first jaw member 24a can be pivoted downward towards the closed position as shown in FIG. 3, thereby applying a compression force to tissue disposed between the first and second jaw members. In addition, a leading edge of the compression member 22 can cut through the tissue, transecting it.

Movement of the compression member 22 can be controlled by the first trigger 14 of the handle portion 2. For example, as the trigger 14 is moved toward the body of the handle portion 2, the compression member 22 can be advanced distally from an initial proximal location of the end effector 6 towards a distal end of the end effector 6. As the compression member 22 traverses the end effector, a first portion of the compression member 22 can engage with a first closure track 32a formed on the first jaw member 24a and a second portion of the compression member 22 can engage with a second closure track 32b located in the second jaw member 24b. The portions of the compression member 22 that engage the closure tracks 32a, 32b can transfer forces from the distal advancement of the compression member 22 into compression forces acting on tissue grasped between the two jaw members 24a, 24b.

As shown in FIGS. 2 and 3, the compression member 22 can, in some embodiments, have an I-beam cross-sectional shape beam that extends along the entire length of the compression member 22. Such a compression member 22 can include a first flat section 22a which can be received in to the first closure track 32a of the first jaw member 24a. The first flat section 22a can have a perpendicular section 22b coupled thereto and extending toward the second jaw member 24b. An opposing end of the perpendicular section 22b can be coupled to a second flat section shown) which mirrors the first flat section 22a and is received within the second closure track 32b of the second jaw member 24b.

Figure 5:
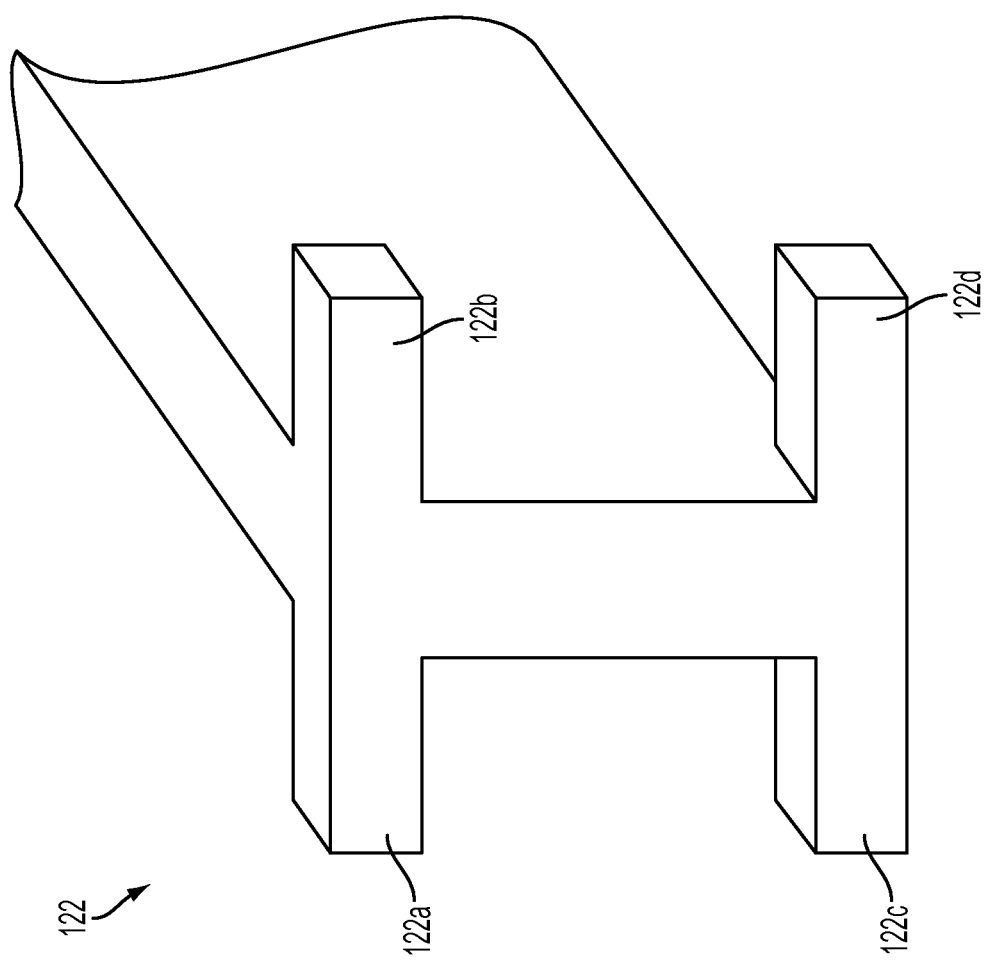
FIG. 5 is a perspective view of one embodiment of a compression member for use in a surgical instrument for cutting and sealing tissue.

FIG. 5 illustrates another embodiment of a compression member 122. The compression member 122 includes an I-beam cross-sectional shape only along a distal portion thereof. The upper portion of the distal end can have an upper left-side flange 122a and an upper right-side flange 122b that do not extend axially along the entire length of the compression member 122. The lower portion of the distal end can include a lower left side flange 122c and a lower right side flange 122d that similarly do not extend axially along the entire length of the compression member 122. The upper left and right side flanges 122a, 122b of the compression member 122 can be received within parallel closure tracks formed in a first jaw member, while the lower left and right side flanges 122c, 122d can be received within closure tracks formed in a second jaw member. As the compression member 122 is advanced through an end effector from a proximal end to a distal end thereof, a distance between the closure tracks in the first and second jaw members can be varied from a large distance to a relatively smaller distance in accordance with the disclosures provided for herein. The fact that the side flanges do not extend along the entire length of the compression member 122 can allow for the application of variable tissue compression by altering the profile of the closure tracks that the flanges ride within the tracks, as described in more detail below.

Figure 6:
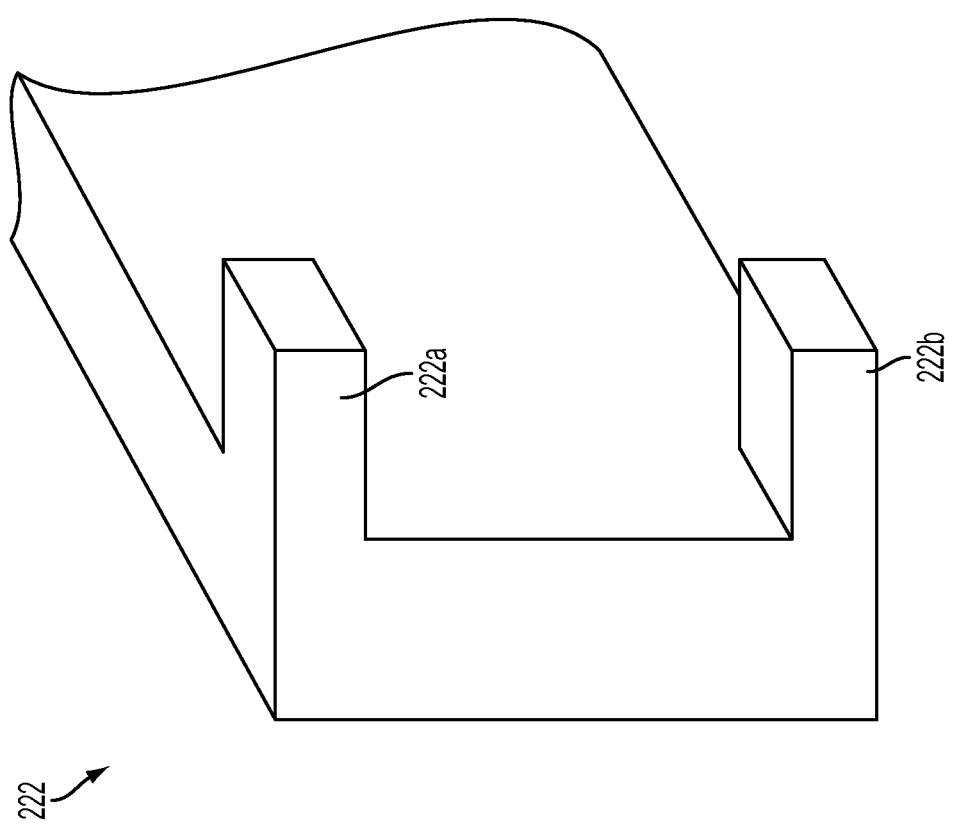
FIG. 6 is a perspective view of an alternative embodiment of a compression member for use in a surgical instrument for cutting and sealing tissue.

Compression members used in combination with the devices and methods of the present invention are not limited to the above-described I-beam shape. FIG. 6, for example, illustrates an alternative embodiment of a compression member 222 having a "C" cross-sectional shape that extends along at least a distal portion of its length. The upper portion of the distal end has a first side flange 222a that does not extend along the entire length of the compression member. The lower portion of the distal end similarly includes a second side flange 222b that can be on the same side as the first side flange 222a and can extend along the compression member for a similar distance as the first side flange 222a. The first side flange 222a of the compression member 222 can be received within a first closure track of a first jaw member and the second side flange 222b can be received within a second closure track of a second jaw member. As the compression member 222 is advanced along the first and second jaw members from a proximal end to a distal end thereof, a distance between the closure tracks in the first and second jaw can be varied from a large distance to a relatively smaller distance in accordance with the disclosures provided for herein. Similar to the embodiment of FIG. 5, the fact that the side flanges do not extend along the entire length of the compression member 222 can allow for the application of variable tissue compression by altering the profile of the closure tracks that the flanges ride within the tracks, as described in more detail below.

Figure 7:
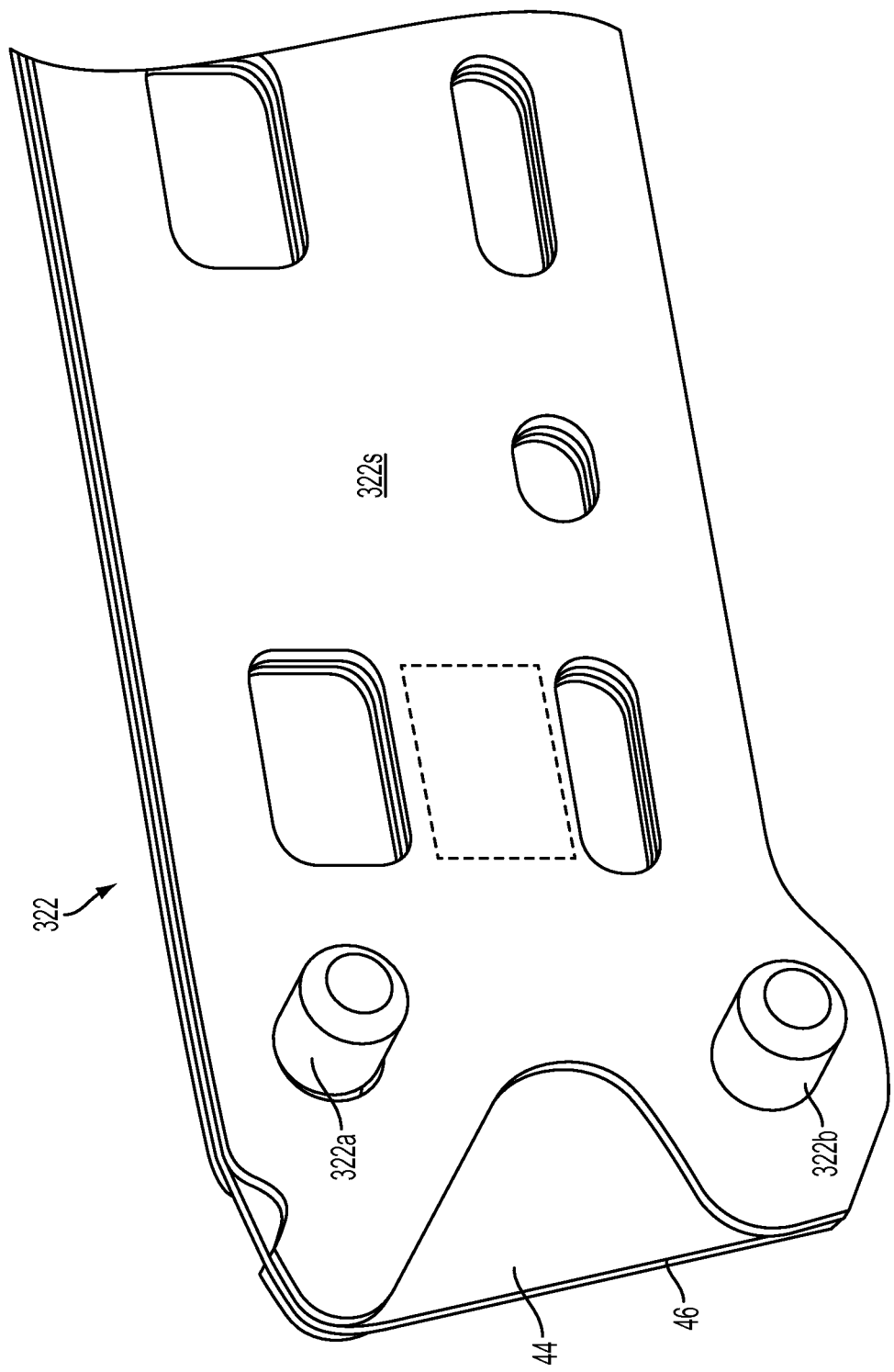
FIG. 7 is a perspective view of another alternative embodiment of a compression member for use in a surgical instrument for cutting and sealing tissue.

In still another exemplary embodiment illustrated in FIG. 7, a compression member 322 can have one or more pins 322a and 322b in place of flanges. Depending on the profile of the closure tracks utilized, the pins 322a and 322b can provide a smoother ride (i.e., lower levels of friction, which can further reduce the force required to actuate the device) along the closure track. Furthermore, in some embodiments the pins 322a and 322b can be configured to rotate and operate as wheels running over the closure tracks of the first and second jaw members. The pins 332a, 332b can extend in a single direction from a surface 322s of the compression member 322 as shown, or alternatively, the pins 332a, 332b can also extend in the opposed direction from an opposed surface (not shown) of the compression member 322, thereby providing a configuration more akin to the I-beam shaped cross-section described above.

FIG. 7 also illustrates a compression member 322 that includes a cutting blade 44 disposed at a distal end thereof. The cutting blade 44 can have a sharp distal cutting edge 46 to efficiently transect tissue as the compression member 322 is advanced along the length of an end effector. The cutting blade 44 can be a separate component mated to the compression member 322 (e.g., held in place by the pins 322a and 322b, as illustrated), or it can be a sharpened distal end of the compression member 322. A cutting blade can be incorporated into any compression member provided for herein or otherwise incorporated into the disclosures provided herein, without departing from the spirit of the present disclosure.

Further information on various aspects of the device 100 can be found in U.S. Patent Publication No. 2012/0083783 to Davison et al., which is hereby incorporated by reference in its entirety, and U.S. patent application Ser. No. 14/075, 839, filed Nov. 8, 2013, and entitled "Electrosurgical Devices," the entire contents of which were previously incorporated by reference herein. Additional details regarding electrosurgical end effectors, jaw closure mechanisms, and electrosurgical energy-delivery surfaces are described in the following U.S. patents and published patent applications, all of which are incorporated by reference in their entirety and made a part of this specification: U.S. Pat. Nos. 7,381, 209, 7,311,709, 7,220,951, 7,189,233, 7,186,253, 7,125,409, 7,112,201, 7,087,054, 7,083,619, 7,070,597, 7,041,102, 7,011,657, 6,929,644, 6,926,716, 6,913,579, 6,905,497, 6,802,843, 6,770,072, 6,656,177, 6,533,784, and 6,500,176, as well as U.S. Patent Publication Nos. 2010/0036370 and 2009/0076506. The various embodiments disclosed in these references can be utilized and combined with the devices and methods described herein.

As mentioned above, one drawback of known tissue transection and sealing devices is that a large amount of force can be required to actuate the device and advance a compression member distally from a proximal end of an end effector. The large amount of force can be required due to the poor mechanical advantage of the compression member when it is positioned close to the connection point of the first and second jaw members. More particularly, tissue captured between the first and second jaw members can act as a spring, resisting the compression forces applied thereto by the first and second jaw members via the compression member. When the compression member is positioned close to the pivot axis of the first and second jaw members, it has a low mechanical advantage and a high level of force is required to compress the tissue. As the compression member is advanced distally away from the pivot axis of the first and second jaw members, its mechanical advantage increases and the force required to advance it further reduces (e.g., similar to how a smaller force applied to a lever far from its fulcrum can counterbalance a larger force applied close to the fulcrum). The devices and methods of the present invention address these and other drawbacks of prior art devices by altering the profile or shape of the closure tracks along which the compression member travels to reduce or modulate the force required to advance the compression member and thereby apply compressive forces to tissue grasped between the first and second jaw members.

Figure 4:
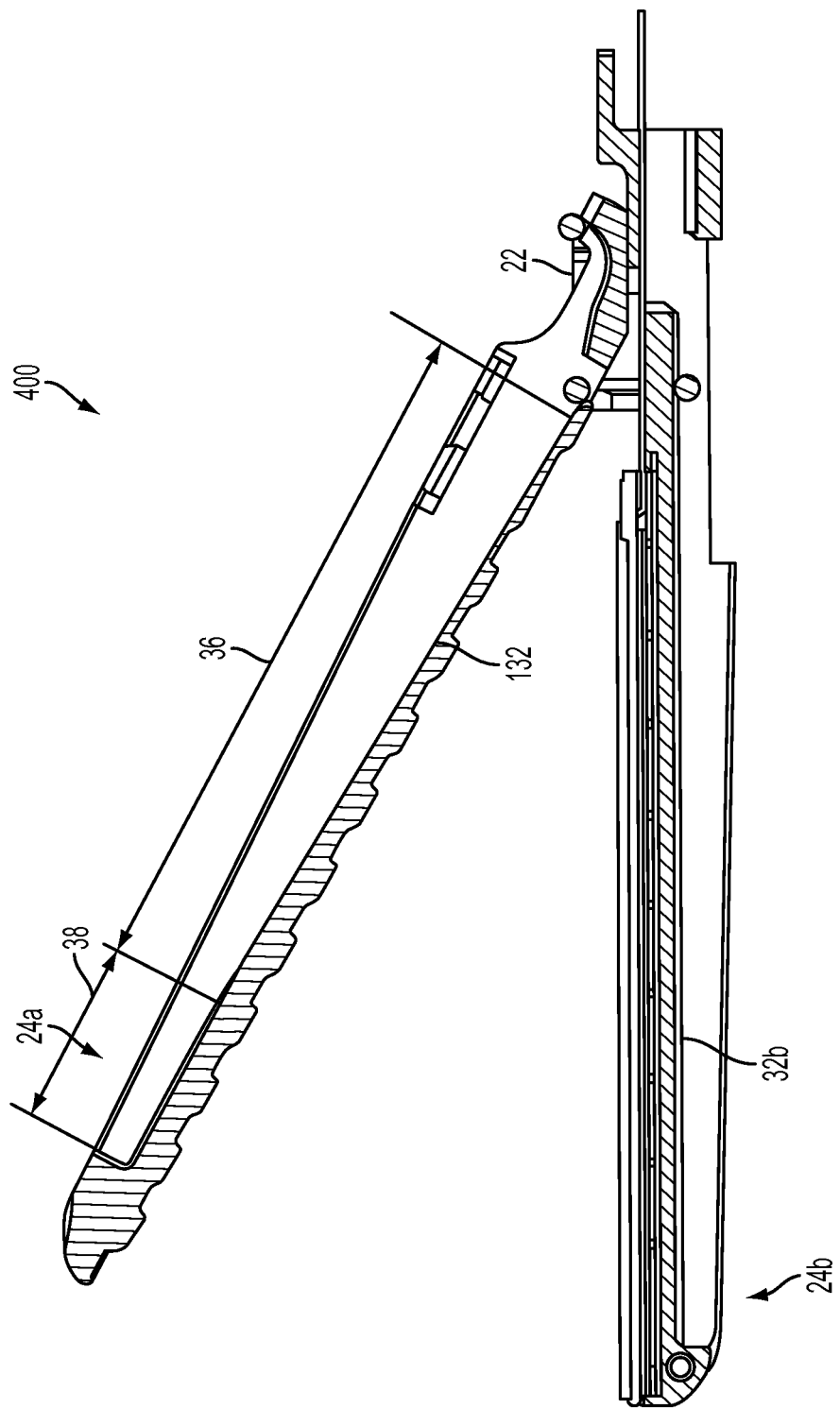
FIG. 4 is a cross sectional view of one embodiment of an end effector for use in a surgical instrument for cutting and sealing tissue.
Figure 8:
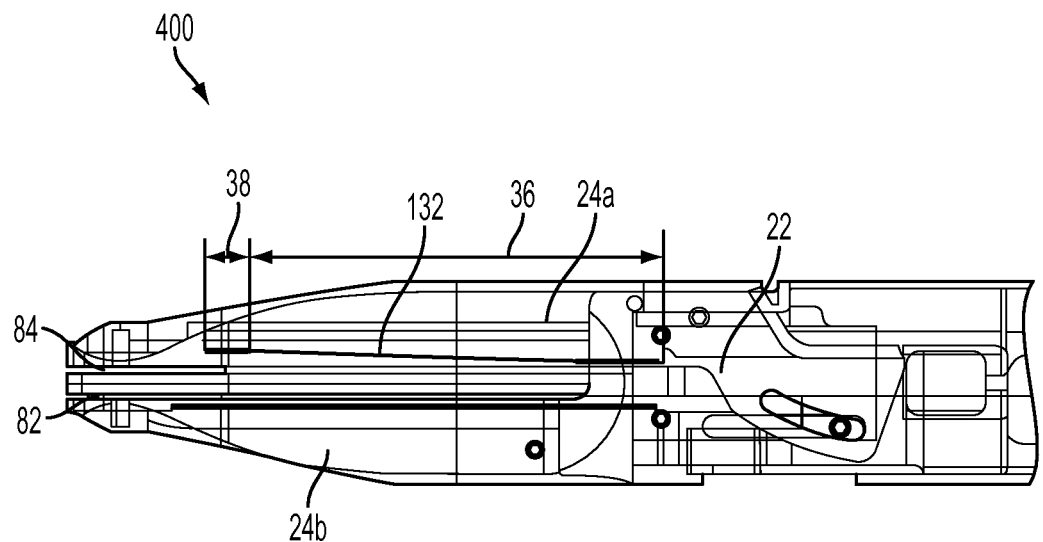
FIG. 8 is a semi-transparent side view of an alternative embodiment of an end effector for use in a surgical instrument for cutting and sealing tissue.
Figure 9:
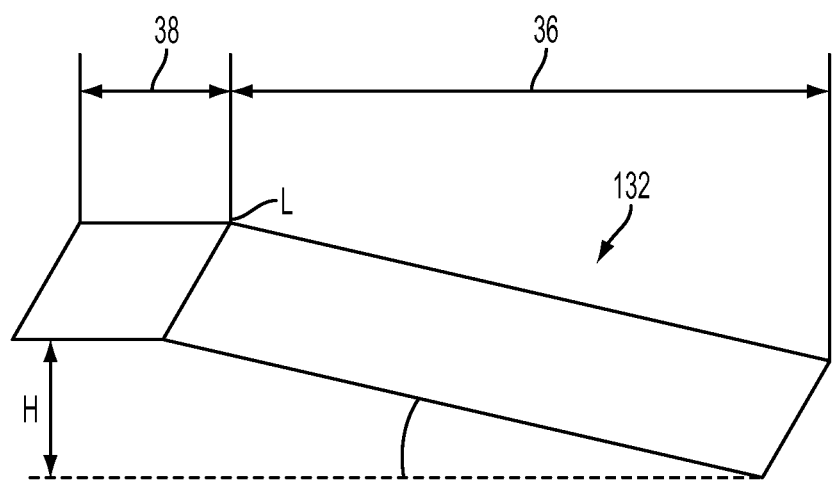
FIG. 9 is a perspective profile view of a closure track of the end effector shown in FIG. 8.

FIGS. 4, 8, and 9 illustrate one embodiment of an end effector 400 according to the teachings of the present invention. The end effector 400 includes a second closure track 32b that extends parallel to a surface of the second jaw member 24b such that a distance between the second closure track 32b and an upper surface 82 of the second jaw member 24b is constant along a length of the second jaw member. In the end effector 6 discussed above, the first closure track 32a in the first jaw member 24a extends similarly and is parallel to the second closure track 32b. Accordingly, a distance between the first and second closure tracks 32a, 32b when the first and second jaw members 24a, 24b are in the closed position is constant along a length of the end effector.

The end effector 400, however, includes a first closure track 132 having a sloped section 36 extending from a proximal end of the closure track 132 to a location adjacent to a distal end of the closure track 132. As shown in FIG. 9, the sloped section 36 continuously increases in height from a starting point to a height H at the location adjacent to the distal end of the closure track 132. The height of the closure track 132 can be measured relative to the lower surface 84 of the first jaw member 24a or relative to the position of the second closure track 32b in the second jaw member 24b when the first and second jaw members are in a closed position (as shown in FIG. 8).

The low starting point and continuously increasing height of the closure track 132 can provide for a decreased actuation force when the compression member 22 is positioned at a proximal end of the end effector 400, i.e., when its mechanical advantage is lowest. The continuously increasing profile allows for an increase in compression force as the compression member's mechanical advantage increases.

Once the compression member 22 has traveled over the first sloped section 36 and reaches a location L adjacent to the distal end of the closure track 132, the compression member can travel along a second distal-most section 38 of the closure track 132. The second distal-most section 38 can be flat relative to the inclined section to ensure that the first and second jaw members are closed to the pre-determined gap distance and that a desired level of compression is exerted on the tissue disposed between the first and second jaw members. In other words, the second distal-most section 38 is a constant distance H from the lower surface of the first jaw 24a or from the second closure track 32b of the second jaw member when in the closed position shown in FIG. 8 (i.e., a distance between the first closure track 132 and the second closure track 32b is constant over the second section 38). As mentioned above, advancing the compression member 22 along the second distal-most section 38 to the distal end of the closure track 132 can ensure that a desired gap and/or compression force is achieved, and complications due to insufficient compression, such as distal tip bleeding, can be reduced.

Figure 10:
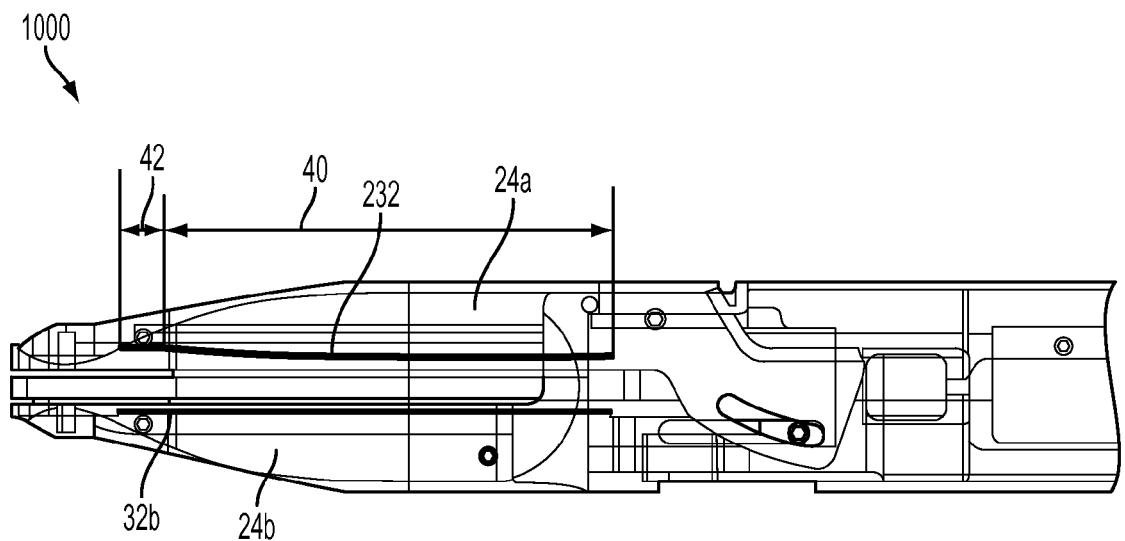
FIG. 10 is a semi-transparent side view of another alternative embodiment of an end effector for use in a surgical instrument for cutting and sealing tissue.
Figure 11:
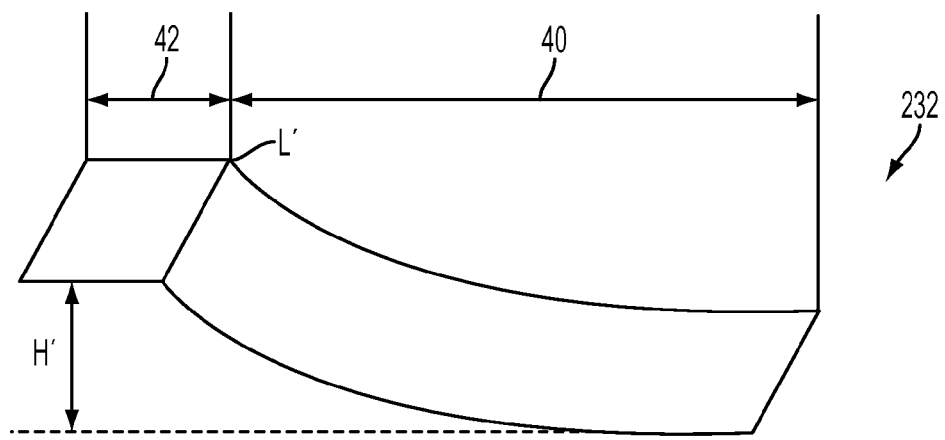
FIG. 11 is a perspective profile view of a closure track of the end effector shown in FIG. 10.

FIGS. 10 and 11 illustrate an alternative embodiment of an end effector 1000 having a continuously increasing or inclined closure track in which the first closure track 232 has gradual upward curvature rather than a linear slope. Similar to the first closure track 132, a profile of the first closure track 232 over a first curved section 40 can increase from a starting point to a height of H' at a location L' adjacent to a distal end of the track, as shown in FIG. 11. The inclusion of a gradual upward curvature in the section 40 can transfer even more compression force to a distal portion of the closure track section 40 where the mechanical advantage of the compression member 22 is greatest than is transferred with the linear slope of the closure track 132 of FIGS. 8 and 9. In certain embodiments, for example, the shape of the curve can be optimally matched to the changing mechanical advantage of the compression member as it advances along the length of the end effector, thereby minimizing the force required to actuate the device.

A second flat distal-most portion 42 of the closure track 232 can meet the curved section 40 at the location L that is adjacent to the distal end of the closure track. Similar to the portion 38 described above, the distal-most portion 42 can maintain a constant desired gap relative to the second closure track 32b, lower surface of the first jaw member 24a, or upper surface of the second jaw member 24b so as to ensure that the jaw members are fully closed to a desired gap distance and compression level. In either embodiment, the force required to translate the compression member 22 from a proximal end of the end effector 400 or 1000 can be reduced due to the altered profile of the first closure track in comparison to profiles of closure tracks in the prior art.

The closure track profiles described herein can have a number of advantages over prior art designs. As already mentioned, providing a decreased distance between the closure tracks of the first and second jaw members at a proximal end of the end effector can reduce the initial force required to actuate the device and delay the application of compression forces until the compression member is located farther from the pivot axis of the first and second jaw members where its mechanical advantage is greater. Some prior art devices, such as those disclosed in U.S. Patent Publication No. 2012/0083783, incorporated by reference above, employ sloped or curved portions of a closure track. However, the devices disclosed in this reference include an initial closure ramp at a proximal end thereof that drives the first and second jaws to a fully closed position before reducing the compression. The location of the initial closure ramp at the proximal-most end of the closure track requires a significant actuation force at precisely the location where the mechanical advantage of the compression member is weakest. Accordingly, the gradual and continuously increasing closure track profiles described herein can have advantages over the prior art in that higher compression forces are delayed until the compression member has advanced sufficiently to increase its mechanical advantage, in turn minimizing the overall force required to actuate the surgical device.

Figure 12:
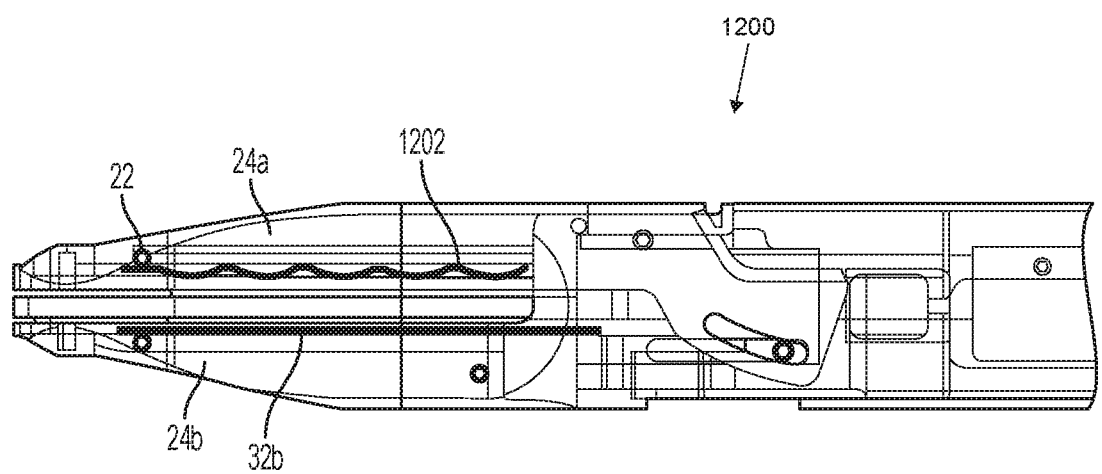
FIG. 12 is a semi-transparent side view of yet another alternative embodiment of an end effector for use in a surgical instrument for cutting and sealing tissue.
Figure 13:
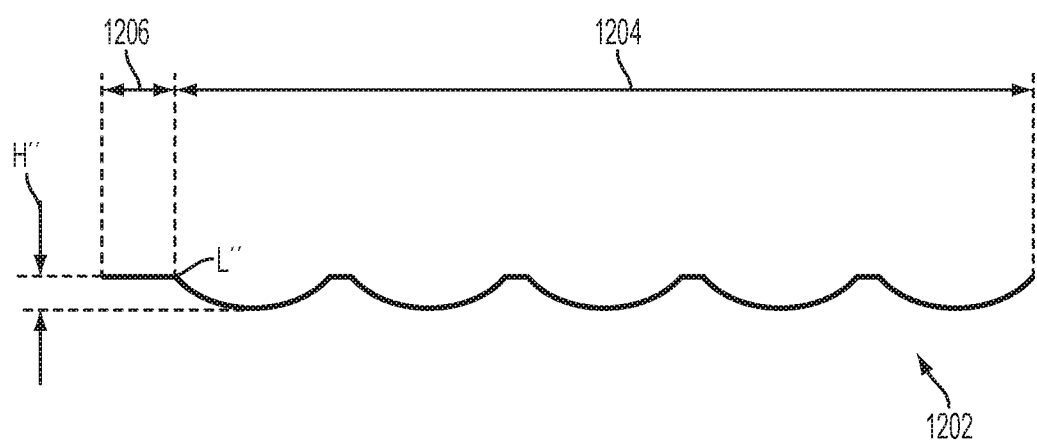
FIG. 13 is a side profile view of a closure track of the end effector shown in FIG. 12.

FIGS. 12 and 13 illustrate still another alternative embodiment of an end effector 1200 having a first closure track 1202 configured to modulate the force required to advance a compression member 22 along the track. As illustrated in FIG. 13, the first closure track 1202 has an alternating profile wherein a distance between the first closure track 1202 and the second closure track 32b when the first and second jaw members 24a, 24b are in a closed position repeatedly alternates between a first distance and a second distance that is greater or less than the first distance, depending on the embodiment. The repeated alternation of the distance between the closure tracks 1202 and 32b can result in repeated alternation of compression forces applied to tissue between a first and second value (where the second value is either higher or lower than the first value, depending on which value corresponds to a peak and which to a valley in the profile). Additionally, in certain embodiments a minimum number of repeated oscillation cycles can be provided over the length of the closure track. For example, in some embodiments a minimum of at least two full alternation cycles (e.g., an increase to a maximum value and a decrease to a minimum value) can be provided. The inclusion of at least two full alternation cycles can more effectively promote tissue sealing, as described in more detail below.

As with the other embodiments described above, the repeatedly alternating profile can continue over a first proximal-most portion 1204 of the first closure track 1202 and can extend from a proximal-most end of the closure track 1202 to a location L" that is adjacent to a distal end of the closure track. A second, flat or constant portion 1206 can extend from the location L" to a distal-most end of the first closure track 1202. Over this second portion 1206, a distance H" between the first closure track 1202 and the second closure track 32b can remain constant so as to ensure a desired gap width or compression level is achieved before actuation is complete. This second portion 1206 is positioned at a distal-most end of the closure track 1202 because it is the greatest distance from the pivot axis of the first and second jaw members 24a, 24b and therefore provides the greatest mechanical advantage for the compression member 22 (and consequently the lowest required user actuation force to achieve the desired compression level).

An alternating closure track profile does not necessarily reduce the initial force required to actuate the device in the same manner as the sloped or curved continuously rising profiles, but can still provide modulation of the required actuation force by temporarily reducing the compression on the tissue. Further, the alternating closure track profile can have particular advantages when used in combination with RF energy delivery to seal tissue. This is because RF energy can cause tissue to partially desiccate as it heats, so as tissue is sealed its volume can be reduced, similar to cooking a beef patty on a grill. The repeated alternation of compression forces on the tissue concurrent with RF energy application can serve to squeeze liquid out of the tissue, similar to pressing a beef patty on a grill with a spatula, thereby further reducing the volume of the tissue between the first and second jaw members. As the volume of tissue decreases, the compression member can more easily be advanced through the tissue. Additionally, the repeated oscillation can allow more time for the RF energy to thoroughly fuse the tissue, thereby creating a better seal.

Figure 14A:
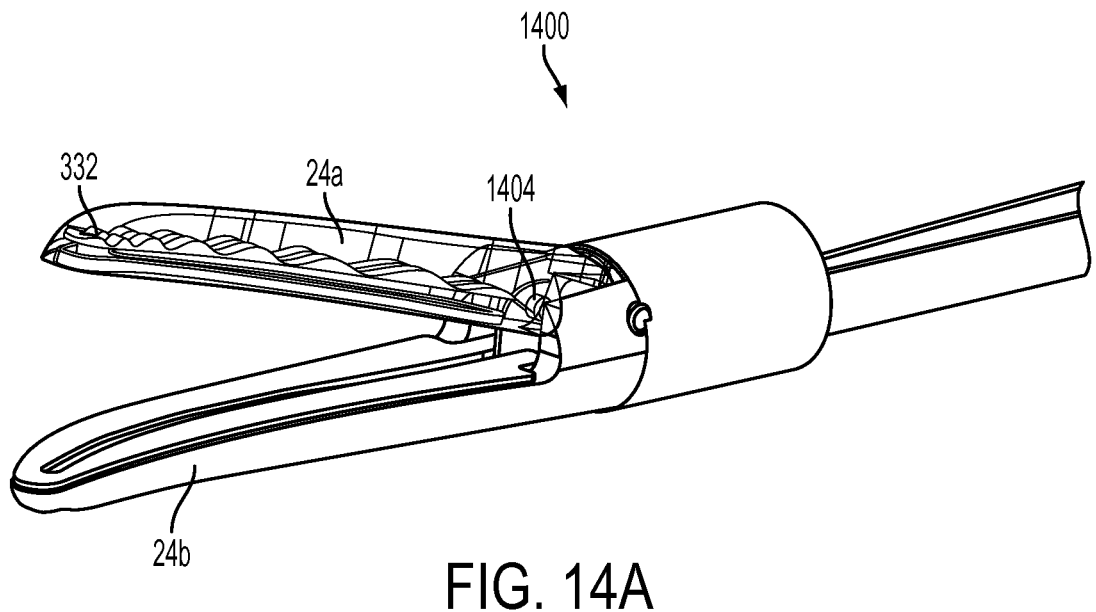
FIG. 14A is a semi-transparent front perspective view of another alternative embodiment of an end effector for use in a surgical instrument for cutting and sealing tissue, the end effector being in an open position.
Figure 14B:
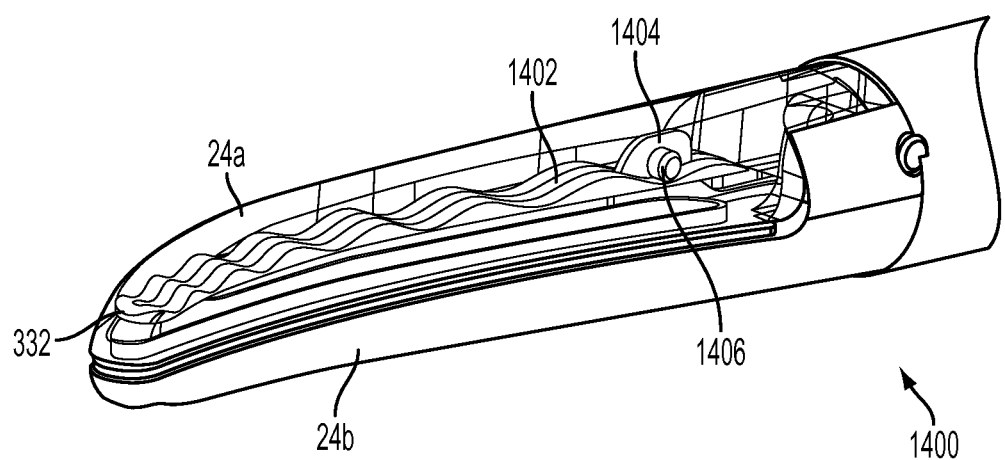
FIG. 14B is a semi-transparent front perspective view of the end effector shown in FIG. 14A in a closed position.
Figure 15:
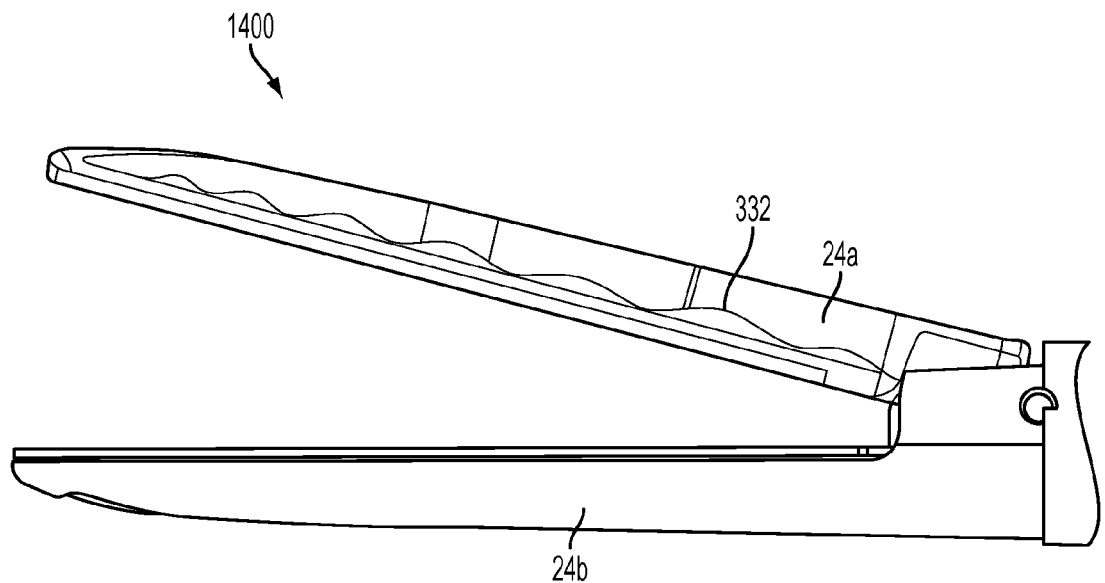
FIG. 15 is a semi-transparent side view of the end effector shown in FIG. 14A.
Figure 16:
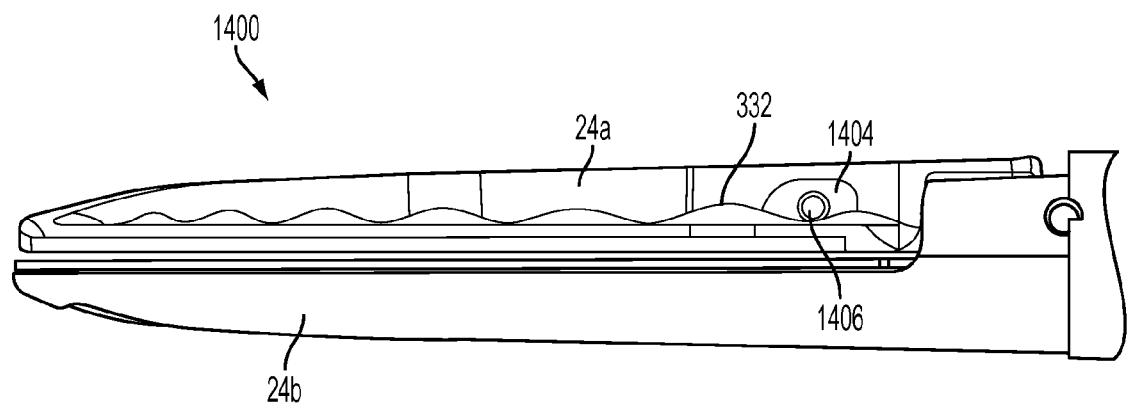
FIG. 16 is a semi-transparent side view of the end effector shown in FIG. 14B.

There are a number of different variations and modifications that can be employed with an alternating closure track profile. FIGS. 14A-17, for example, illustrate one embodiment of an end effector 1400 in which a first closure track 332 has an irregularly alternating profile. More particularly, the closure track 332 can have a profile similar to a wave function in which the wavelength decreases from a proximal end to a distal end of the end effector 1400. Referring to FIGS. 14A and 14B, a perspective view of the first closure track 332 extending along the first jaw member 24a is illustrated. The figure shows that the first closure track 332 is formed on either side of a compression member channel 1402 that extends along a length of the first jaw member 24a. A compression member 1404, similar to the compression member 322 discussed above, is slidably disposed within the channel 1402 and includes at least one protrusion 1406 that rides along the first closure track 332. Because the compression member 1404 also includes a protrusion riding along a second closure track (not shown) in the second jaw member 24b, the compression member 1404 is prevented from moving vertically within the plane of the first and second jaw members (i.e., in a direction perpendicular to a longitudinal axis of the end effector, or the up/down directions of FIGS. 14A and 14B). Accordingly, as the compression member 1404 is advanced along the length of the end effector, the interaction between the protrusion 1406 and the first closure track 332 will cause the first jaw member 24a to pivot relative to the second jaw member 24b, thereby exerting differing levels of compression on tissue disposed between the first and second jaw members. FIGS. 15 and 16 illustrate the embodiment shown in FIGS. 14A and 14B from a side perspective, again showing how the protrusion 1406 formed on the compression member 1400 rides along the first closure track 332 and causes relative movement between the first and second jaw members 24a, 24b.

Figure 17:
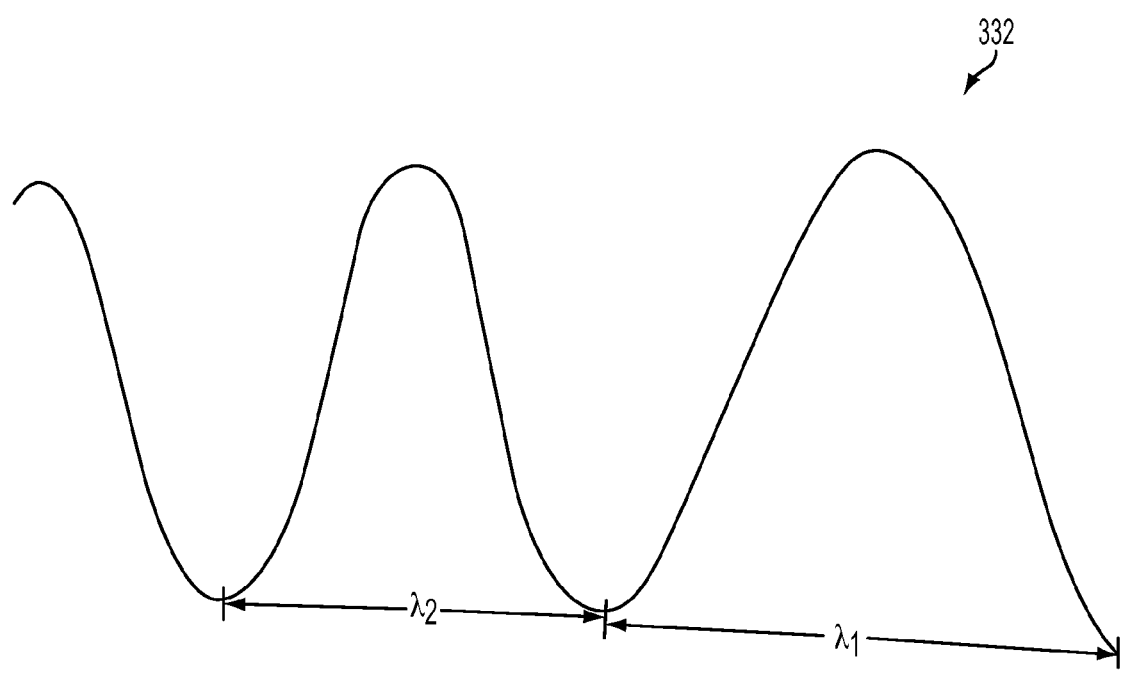
FIG. 17 is a side profile view of one embodiment of a closure track for use in an end effector of a surgical instrument for cutting and sealing tissue.

Returning to the concept of irregular alternation introduced above, FIG. 17 illustrates an embodiment of a closure track profile in which a wavelength λ1 is larger than each subsequent wavelength, λ2, λ3, etc. Other combinations of wavelengths can also be incorporated into such an embodiment, and thus in other embodiments some subsequent wavelengths can be shorter, longer, or the same size as preceding wavelengths.

Figure 18:
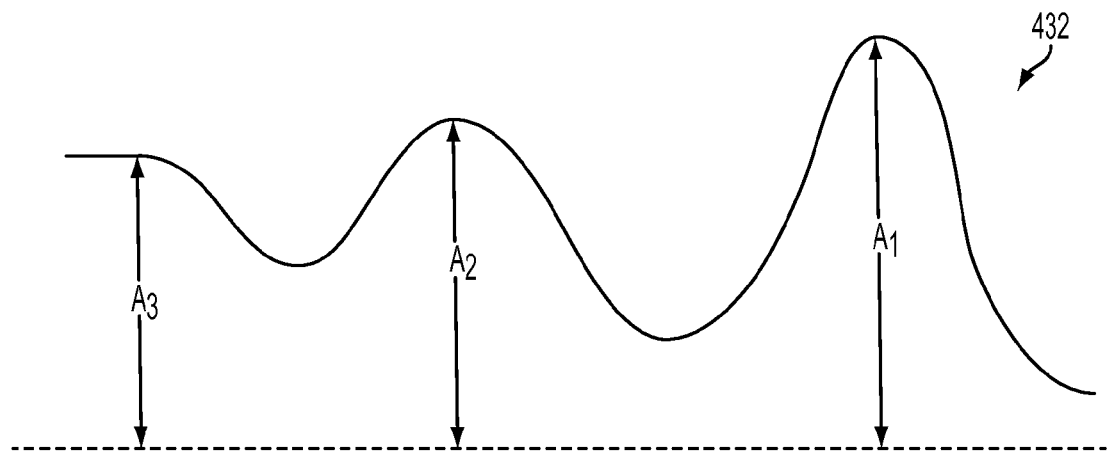
FIG. 18 is a side profile view of an alternative embodiment of a closure track for use in an end effector of a surgical instrument for cutting and sealing tissue.

In another embodiment shown in FIG. 18, a closure track 432 can have an alternating profile similar to a wave function in which the amplitude increases or decreases with each successive oscillation (i.e., the amplitude can either increase or decrease from a proximal end of the end effector to a distal end of the end effector). In other words, a distance between the first closure track and the second closure track can repeatedly alternate between any number of values (e.g., three, four, etc.) and each successive value can be greater or less than the preceding values. In such an embodiment, the closure track 432 can have a constant wavelength, or it can have a variable wavelength similar to the closure track 332 discussed above. As shown in FIG. 18, the amplitude height A1 is larger than that of each subsequent amplitude A2, A3, etc. Other combinations of amplitudes can also be incorporated into such an embodiment, and thus in other embodiments some subsequent amplitudes can be smaller, larger, or the same size as preceding amplitudes.

Figure 19:
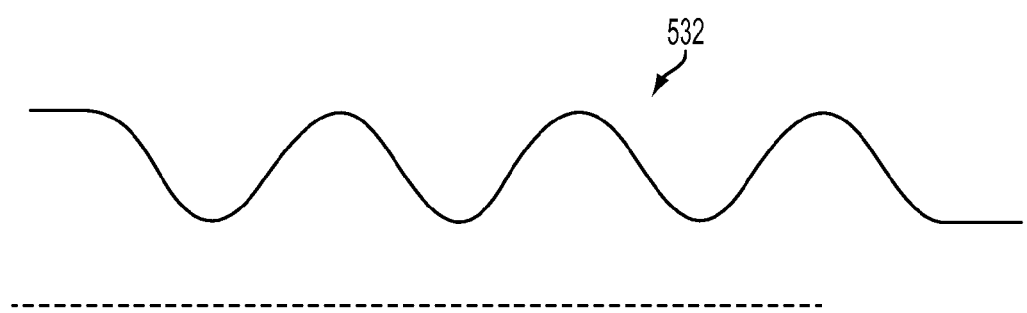
FIG. 19 is a side profile view of another alternative embodiment of a closure track for use in an end effector of a surgical instrument for cutting and sealing tissue.

In still another exemplary embodiment shown in FIG. 19, a closure track 532 can have an alternating profile similar to a sinusoidal wave function wherein the wavelength and amplitude is substantially constant over the length of the closure track. In any of these embodiments, the amount of compression between the first and second jaws can oscillate as a function of the distance between the first closure track and the second closure track when the compression member traverses the track.

As described above, the alternating track profiles shown in FIGS. 12-19 can have an additional benefit of increasing tissue seal quality in applications where RF energy delivery is used. This is because the compression of the first jaw member 24a against the second jaw member 24b can be higher at a peak of each oscillation, which can allow the jaws to push excess fluids out of the tissue. Conversely, the compression of the first jaw member against the second jaw member can be lower at a valley of each oscillation, which can allow the RF energy to heat the tissue and thereby make it easier to compress. The alternating levels of tissue compression provided by the alternating closure track profiles can allow for a more effective sealing of tissue than is otherwise possible.

Finally, and as noted above, the second closure track 32b in any of these embodiments can have either a flat or constant profile as known in the art, or can include one or more sloped, curved, or alternating profiles similar to the first closure tracks described above. In other words, a distance between a second closure track 32b and an upper surface 82 of a second jaw member 24b can be constant from a proximal end of the closure track to a distal end of the closure track, or the distance can vary along the length of the closure track in any of the manners described herein. Indeed, to the extent any alternating profile provided for herein is illustrated with one particular embodiment, a person having skill in the art can incorporate such profiles into other embodiments provided for herein or otherwise known to those skilled in the art.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A surgical end effector, comprising:
   first and second jaw members movable relative to one another between an open position and a closed position to clamp tissue therebetween;
   a first closure track formed in the first jaw member and extending along a length thereof;
   a second closure track formed in the second jaw member and extending along a length thereof; and
   a compression member configured such that a first portion of the compression member contacts the first closure track at a proximal-most end of the first closure track when the compression member is at a proximal-most position and a second portion of the compression member contacts the second closure track, the compression member being further configured to translate longitudinally along a length of the end effector to move the first jaw member and the second jaw member so as to apply compression to tissue disposed between the first and second jaw members as the compression member advances from the proximal-most position towards a distal end of the end effector;
   wherein, when the first and second jaw members are in the closed position, a distance between the first closure track and the second closure track increases continuously from the proximal-most end of the first closure track to a location adjacent to a distal end of the first closure track.

2. The end effector of claim 1, wherein the distance between the first closure track and the second closure track remains constant from the distal end of the first closure track to the location adjacent to the distal end of the first closure track.

3. The end effector of claim 1, wherein at least one of the first and second jaw members includes at least one electrode disposed on a surface thereof that is configured to contact tissue clamped between the first and second jaw members.

4. The end effector of claim 1, wherein the distance between the first closure track and the second closure track increases linearly from the proximal-most end of the first closure track to the location adjacent to the distal end of the first closure track.

5. The end effector of claim 1, wherein a profile of the distance between the first closure track and the second closure track from the proximal-most end of the first closure track to the location adjacent to the distal end of the first closure track is curved.

6. The end effector of claim 1, wherein a distance between the second closure track and a surface of the second jaw member that faces the first jaw member remains constant from a proximal-most end of the second closure track to a distal end of the second closure track.

7. The end effector of claim 1, wherein a distance between the second closure track and a surface of the second jaw member that faces the first jaw member varies from a proximal-most end of the second closure track to a distal end of the second closure track.

8. The end effector of claim 7, wherein a profile of the distance between the second closure track and the surface of the second jaw member includes at least one sloped or curved portion.

9. A surgical end effector, comprising:
   first and second jaw members movable relative to one another between an open position and a closed position to clamp tissue therebetween;
   a first closure track formed in the first jaw member and extending along a length thereof;
   a second closure track formed in the second jaw member and extending along a length thereof; and
   a compression member configured to translate longitudinally along a length of the end effector such that a first portion of the compression member contacts the first closure track and a second portion of the compression member contacts the second closure track;
   wherein a profile of at least one of the first closure track and the second closure track is a wave function to vary an amount of compression applied to the tissue clamped between the first and second jaw members;
   wherein the wave function includes a plurality of full alternation cycles wherein a distance between the first closure track and the second closure track alternates between at least a first distance and a second distance.

10. The end effector of claim 9, wherein the profile of at least one of the first closure track and the second closure track is a wave function having constant amplitude and frequency.

11. The end effector of claim 9, wherein the profile of at least one of the first closure track and the second closure track is a wave function having at least one of variable amplitude and variable frequency.

12. The end effector of claim 11, wherein the profile of at least one of the first closure track and the second closure track is a wave function having both variable amplitude and variable frequency.

13. The end effector of claim 9, wherein the distance between the first closure track and the second closure track remains constant from a distal end of the first closure track to a location adjacent to the distal end the first closure track.

14. The end effector of claim 9, wherein the distance between the first closure track and the second closure track alternates regularly between the first distance and the second distance.

15. The end effector of claim 9, wherein the distance between the first closure track and the second closure track repeatedly alternates between the first distance, the second distance, and a third distance along the length of the end effector, wherein the third distance is greater than the second distance and the first distance.

16. A method for actuating a surgical instrument, comprising:
   positioning an end effector having first and second jaw members such that tissue is disposed within a gap between the first and second jaw members;
   advancing a compression member from a proximal-most position toward a distal end of the end effector, wherein, at the proximal-most position, the compression member contacts a proximal-most end of a first closure track formed in the first jaw member and a second closure track formed in the second jaw member;

wherein a distance between the first closure track and the second closure track increases continuously from the proximal-most end of the first closure track to a location adjacent to a distal end of the first closure track such that advancing the compression member from the proximal-most position toward the distal end of the end effector applies a continuously variable compression force to the tissue.

17. The method of claim 16, further comprising advancing the compression member distally from the location adjacent to a distal end of the first closure track toward the distal end thereof;

wherein a distance between the first closure track and the second closure track remains constant from the location adjacent to the distal end of the first closure track to the distal end thereof such that advancing the compression member applies a constant compression force to the tissue.

18. The method of claim 16, further comprising delivering energy into the tissue from at least one electrode coupled to the end effector to seal the tissue.

* * * * *